United States Patent
Poindexter et al.

(10) Patent No.: US 6,916,812 B2
(45) Date of Patent: Jul. 12, 2005

(54) ALPHA-AMINOAMIDE DERIVATIVES AS MELANOCORTIN AGONISTS

(75) Inventors: Graham S. Poindexter, Old Saybrook, CT (US); Guanglin Luo, Madison, CT (US); Ling Chen, Middletown, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 181 days.

(21) Appl. No.: 10/264,709

(22) Filed: Oct. 4, 2002

(65) Prior Publication Data

US 2003/0232807 A1 Dec. 18, 2003

Related U.S. Application Data

(60) Provisional application No. 60/327,961, filed on Oct. 9, 2001.

(51) Int. Cl.[7] ............... A61K 31/495; A61K 31/496; C07D 295/192; C07D 405/10; C07D 409/10
(52) U.S. Cl. ............... 514/235.8; 514/253.01; 514/254.09; 514/254.1; 514/255.01; 514/253.06; 514/254.05; 514/254.08; 514/254.11; 514/218; 544/121; 544/360; 544/363; 544/364; 544/370; 544/373; 544/372; 544/376; 544/377; 544/379; 544/380; 544/391; 540/575
(58) Field of Search ............... 544/360, 373, 544/377, 379, 380, 391, 121, 363, 364, 372, 370, 376; 514/253.01, 254.09, 254.1, 255.01, 235.8, 253.06, 254.05, 254.08, 254.11

(56) References Cited

U.S. PATENT DOCUMENTS 5,885,999 A 3/1999 Elliott et al.
2004/0053933 A1 * 3/2004 Pontillo et al. ........ 514/252.02

FOREIGN PATENT DOCUMENTS

WO WO 99/64002 12/1999
WO WO 00/74679 12/2000

OTHER PUBLICATIONS

Andersson et al. Expert Opin. Ther. Patents, vol. 11, pp. 1583–1592 (2001).*
Sebhat et al. Annual Reports in Medicinal Chemistry, vol. 38, pp. 31–40 (2003).*
Chen, W. et al., "Exocrine Gland Dysfunction in MC5–R–Deficient Mice: Evidence for Coordinated Regulation of Exocrine Gland Function by Melanocortin Peptides", Cell 91, pp. 789–798 (Dec. 1997).
Chhajlani, V. and Wikberg, J.E.S., "Molecular cloning and expression of the human melanocyte stimulating hormone receptor cDNA", J.E., FEBS Lett., 309(3), pp. 417–420 (Sep. 1992).
Dorr, R.T., et al., "Evaluation of Melanotan–II, A Superpotent Cyclic Melanotropic Peptide in a Pilot Phase–I Clinical Study", Life Sciences, 58(20), pp. 1777–1784 (1996).
Huszar, D., et al., "Targeted Disruption of the Melanocortin–4 Receptor Results in Obesity in Mice", Cell, 88, pp. 131–141 (Jan. 1997).
Mountjoy, K.G. et al., "The Cloning of a Family of Genes that Encode the Melanocortin Receptors", Science, 257, pp. 1248–1251 (1997).
Wessells, H. et al., "Synthetic Melanotropic peptide Initiates Erections in Men with Psychogenic Erectile Dysfunction: Double–blind, Placebo Controlled Crossover Study", J. Urology, 160, pp. 389–393 (1998).
Yen, T.Y. et al., "Obesity, diabetes, and neoplasia in yellow $A^{vy}$/–mice: ectopic expression of the agouti gene", The FASEB J, 8, pp. 479–488 (1994).

* cited by examiner

Primary Examiner—Emily Bernhardt
(74) Attorney, Agent, or Firm—Aldo A. Algieri

(57) ABSTRACT

Novel piperazine and homopiperazine derivatives are agonists of melanocortin receptor(s) and are useful for the treatment, control, or prevention of diseases and disorders responsive to the activation of the melanocortin receptors. The compounds of the present invention are therefore useful for treatment or prevention of diseases and disorders such as obesity, diabetes, and sexual dysfunction.

7 Claims, No Drawings

ALPHA-AMINOAMIDE DERIVATIVES AS MELANOCORTIN AGONISTS

CROSS-REFERENCE TO RELATED APPLICATIONS

This is a non-provisional application which claims the benefit of U.S. Provisional Application No. 60/327,961 filed Oct. 9, 2001.

FIELD OF THE INVENTION

This invention relates to tyrosinamide compounds which act as melanocortin receptor agonists, and as such are useful in the treatment or prevention of diseases and disorders responsive to the activation of melanocortin receptors, such as obesity, diabetes and sexual dysfunction. This invention also relates to pharmaceutical compositions of the tyrosinamide compounds and methods of treating or preventing diseases and disorders responsive to the activation of melanocortin receptors in mammals.

BACKGROUND OF THE INVENTION

Pro-opiomelanocortin (POMC) derived peptides are known to affect food intake. There also exists evidence that the G-protein coupled receptors of the melanocortin receptor (MC-R) family are targets of POMC derived peptides involved in the control of food intake and metabolism. The melanocortin receptors may therefore be viable targets for the control of obesity.

At least five MC-Rs have been identified, and these receptors are expressed in different tissues. MC-1R is primarily expressed in melanocytes [Chhajlani, V.; Wikberg, J. E., *FEBS Lett.*, 309 (1997) 417–420; Mountjoy, K. G. et al., *Science*, 257 (1997) 1248–1251]. MC-2R is expressed in the adrenal cortex and represents the ACTH receptor [Mountjoy, K. G. et al., *Science*, 257 (1997) 1248–1251]. MC-3R is expressed in the brain, gut, and placenta and may be involved in the control of food intake and thermogenesis. MC-4R, is a seven-transmembrane receptor which is expressed in the brain, and its inactivation has been shown to cause obesity [Huszar, D. et al., *Cell,* 88 (1997) 131–141]. MC-5R is expressed in various tissues including white fat, placenta, exocrine glands and brain and inactivation of this receptor results in decreased production of lipids from the sebaceous glands which in turn effects thermoregulation [Chen, W. et al., *Cell,* 91 (1997). 789–798].

Evidence for the involvement of MC-Rs in obesity includes the agouti mouse. The viable yellow ($A^{vy}$) variants of agouti mice express the agouti protein, both ectopically and within the hair follicle, which acts as an antagonist of the MC-1R, MC-3R, and MC-4R. These mice are characterized by maturity-onset obesity, hyperinsulinemia, hyperglycemia in males, yellow coat color, hyperphagia, increased rates of hepatic lipogenesis and decreased rates of lipolysis in adipocytes [Yen, T. Y. et al., *The FASEB J,* 8 (1994) 479–488] and references therein) indicating that blocking the action of the MC-1R, MC-3R, and MC-4R can lead to the characteristics of the pleiotropic obesity syndrome. MC-4R knockout mice exhibit the same phenotype as the agouti ($A^{vy}$) mice and have other characteristics of the pleiotropic obesity syndrome described above [Huszar, D. et al., *Cell,* 88 (1997) 131–141]. Rodents injected intracerebroventricularly (ICV) with the cyclic heptapeptide melanotan-II (MT-II), a MC-1R, -3R, -4R, -5R agonist, have reduced food intake in several animal feeding models (NPY, ob/ob, agouti, fasted) while ICV injected SHU-9119, a MC-3R, -4R antagonist and MC-1R, -5R agonist, reverses this effect and can induce hyperphagia [Nargund, R. et al., WO 99/64002, published Dec. 16, 1999]. Additionally, chronic intraperitoneal treatment of Zucker fatty rats with an α-NDP-MSH derivative (HP228) has been reported to activate MC-1R, -3R, -4R and -5R and to attenuate food intake and body weight gain over a 12 week period [Nargund, R. et al. WO 99/64002, published December 16, 1999].

Melanocortin receptors may also be viable targets for the control of certain types of sexual dysfunction. Intramuscular administration of melanotan-II (MT-II) within a dose range of 0.005–0.03 mg/kg caused intermittent non-painful penile erections in three normal male volunteers for a period of 1–5 hours after dosing [Dorr et al., *Life Sciences,* 58(20) (1996) 1777–1784]. Subcutaneous administration of MT-II (0.025 mg/kg and 0.1 mg/kg) to 10 patients with psychogenic erectile dysfunction caused transient erections (8 responders) with onset from 50–180 minutes [Wessells, H. et al., *J. Urology,* 160 (1998) 389–393].

Spiropiperidine derivatives, of the following general Formula (i), which act as melanocortin receptor agonists were disclosed by Nargund et al. in WO 99/64002 (published on Dec. 16, 1999).

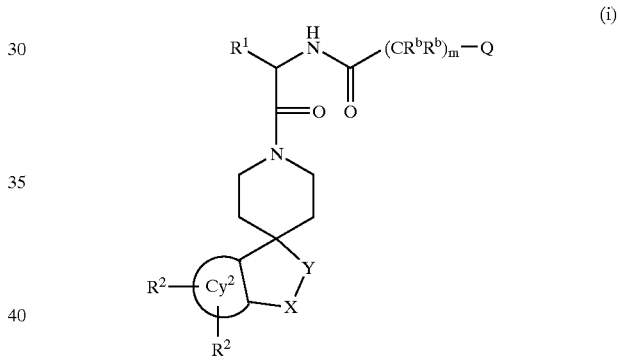

(i)

Piperidine derivatives of general Formula (ii) which act as selective melanocortin-4 receptor agonists useful for the treatment, control or prevention of obesity, diabetes and sexual dysfunction were disclosed by Bakshi, et al. In WO 00/74679 (published on Dec. 14, 2000).

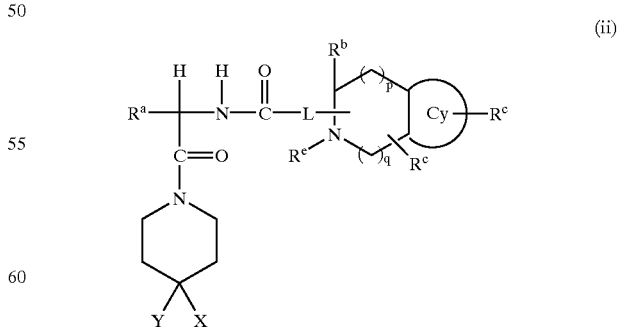

(ii)

Serine derivatives, described as useful for the treatment or prevention of pain, inflammation, migraine, emesis and postherpetic neuralgia were disclosed by Elliott et al. in U.S.

Pat. No. 5,885,999 (issued Mar. 23, 1999). These derivatives are of the general Formula (iii), shown below,

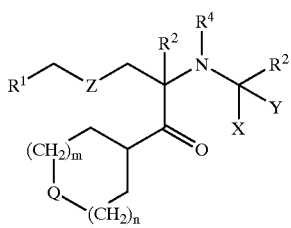

(iii)

wherein m is 0, 1, or 2; and n is 0 or 1, with the proviso that the sum of m and n is 1 or 2; $R^1$ represents phenyl, napthyl, benzhydryl or benzyl; $R^2$ represents hydrogen, phenyl, napthyl, benzhydryl, benzyl, indazolyl, thienyl, furanyl, pyridyl, thiazolyl, tetrazolyl and quinolinyl; $R^3$ and $R^4$ each independently represent hydrogen or $C_{1-6}$alkyl, or $R^3$ and $R^4$ together are linked so as to form a $C_{1-3}$ alkylene chain; Q represents $CR^5R^6$ or $NR^5$; X and Y each independently represents hydrogen, or together form a group =O; and Z represents a bond, O, S, SO, $SO_2$, $NR^c$ or —$(CR^cR^d)$—, where $R^c$ and $R^d$ each independently represent hydrogen or $C_{1-6}$alkyl.

These reference compounds are distinguished structurally from the compounds of the instant invention by virtue of these art compounds containing an amide or serine linked substituted piperidine moiety whereas the compounds of the instant invention contain a tyrosinamide linked substituted piperazine moiety. The novel compounds of the present invention have also been discovered to possess melanocortin receptor activity, thus, the prior art does not disclose nor suggest the unique combination of structural fragments which embody these novel tyrosinomide derivatives as having good activity at melanocortin receptor sites.

SUMMARY OF THE INVENTION

The present invention relates to novel tyrosinamide derivatives having the general Formula I

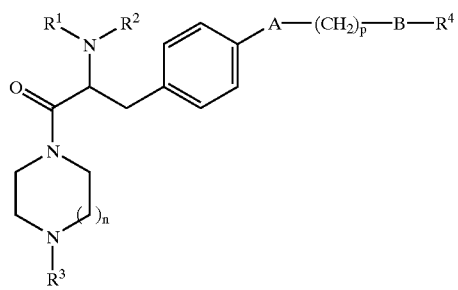

I wherein A, B, $R^1$, $R^2$, $R^3$, $R^4$, n and p are as defined below or a pharmaceutically acceptable salt thereof. The present invention also provides pharmaceutical compositions comprising said derivatives and a pharmaceutically acceptable carrier or diluent and to a method of treating or preventing diseases and disorders responsive to the activation of melatonocortin receptors in mammals.

DETAILED DESCRIPTION OF THE INVENTION

The present invention provides novel tyrosinamide compounds, pharmaceutical compositions, and methods of treating or preventing diseases and disorders responsive to the activation of melanocortin receptors in mammals.

The present invention provides compounds of Formula I, or a pharmaceutically acceptable salt thereof

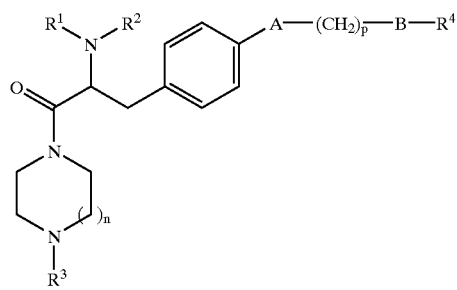

I wherein
n is 1 or 2;
p is selected from an integer of 0 to 4;
A is a bond or O;
B is selected from the group consisting of a bond, O, S, NH and —$N(C_{1-4})$alkyl;
$R^1$ and
$R^2$ each are independently selected from the group consisting of hydrogen, $(C_{1-4})$alkyl, phenyl$(C_{1-4})$alkyl, imidazolyl$(C_{1-4})$alkyl, imidazolyl$(C_{1-4})$alkylcarbonyl, imidazolylcarbonyl, morpholinyl$(C_{1-4})$alkyl, piperidinyl $(C_{1-4})$alkyl, and di$(C_{1-4})$alkylamino$(C_{1-4})$alkyl;
$R^3$ is selected from the group consisting of $(C_{1-8})$alkyl,

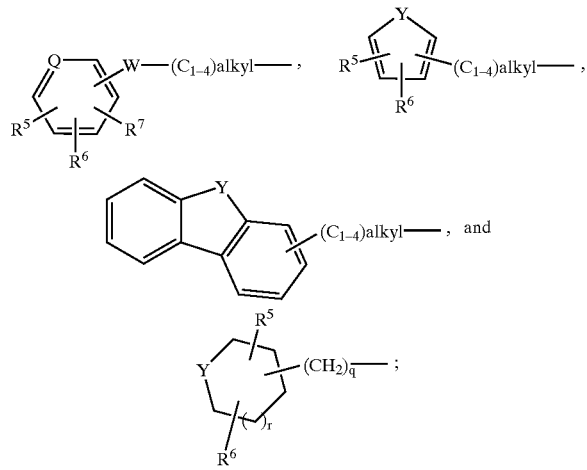

Q is N or $CR^8$;
W is selected from the group consisting of a bond, NH, O, S, and $C_6H_5CH$;
Y is selected from the group consisting of $CHR^{11}$, $NR^{11}$, O, and S;
q is 0 or 1;
r is 0 or 1;
$R^4$ is selected from the group consisting of $C_{1-4}$alkyl, $C_{3-7}$cycloalkyl, phenyl, phenyl$(C_{1-4})$alkyl, napthalenyl, benzodioxolyl, benzodioxanyl, pyridinyl, quinolinyl, thienyl, benzothienyl, dibenzothienyl, and phenoxathiinyl; and wherein said phenyl, thienyl and pyridyl are optionally substituted with one to three substituents each independently selected from halogen, trifluoromethyl, trifluoromethoxy, nitro, $C_{1-4}$alkyl, $C_{1-4}$alkoxy, $C_{1-4}$thioalkoxy, $C_{1-4}$alkylcarbonyl, di$(C_{1-4}$alkyl)amino, amino, carboxyl, phenyl, phenyl($C_{1-4}$)alkyl, phenyloxy, and phenylmethoxy;

$R^5$, $R^6$, $R^7$ and $R^8$ each are independently selected from the group consisting of hydrogen, halogen, $C_{1-8}$alkyl, trifluoromethyl, nitro, $XR^9$, phenyl, and phenyl($C_{2-6}$)alkenyl, wherein said phenyl is optionally substituted with one to two halogen or nitro groups; or any two variables selected from the group consisting of $R^5$, $R^6$, $R^7$ and $R^8$, when attached to adjacent carbon atoms in a ring containing Q or Y and taken together can be —$OCH_2O$—, —$O(CH_2)_2O$—, —CH=CH—CH=CH—, or —CH=CH—N($R^{11}$)—;

X is selected from the group consisting of $NR^{10}$, O, and $S(O)_m$, wherein m is 0, 1, or 2;

$R^9$ is selected from the group consisting of hydrogen, $C_{1-8}$alkyl, phenyl, phenyl($C_{1-4}$)alkyl, and wherein said phenyl and phenyl($C_{1-4}$)alkyl are optionally substituted with one to three substituents each independently selected from nitro, trifluoromethyl, halogen and $C_{1-4}$alkyl;

$R^{10}$ is selected from the group consisting of hydrogen, $C^{1-8}$alkyl, and phenyl; and $R^{11}$ is selected from the group consisting of hydrogen, $C_{1-4}$alkyl, $C_{1-4}$alkylsulfonyl, phenyl, phenyl($C_{1-4}$)alkyl, and phenylsulfonyl, wherein said phenyl, phenyl($C_{1-4}$) alkyl, and phenylsulfonyl are optionally substituted with one to three substituents each independently selected from $C_{1-4}$alkyl or halogen.

The present invention also provides a method for the treatment of or protection from diseases, disorders and conditions responsive to the activation of melanocortin receptors in a mammal in need thereof, which comprises administering to said mammal a therapeutically effective amount of a compound of Formula I or a pharmaceutically acceptable salt thereof. Preferably, the compounds of Formula I are useful in the treatment of obesity, diabetes and sexual dysfunction.

The compounds of the present invention may possess asymmetric centers and therefore the present invention is intended to include the racemate as well as the individual enantiomeric forms of the compounds of Formula I as described herein and in the claims and mixtures thereof.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like.

"Halogen" refers to chlorine, bromine, iodine or fluorine.

An "alkyl" group refers to a saturated aliphatic hydrocarbon including straight chain and branched chain groups. Preferably, the alkyl group has 1 to 20 carbon atoms (whenever a numerical range; e.g., "1–8", is stated herein, it means that the group, in this case the alkyl group may contain 1 carbon atom, 2 carbon atoms, 3 carbon atoms, etc. up to and including 8 carbon atoms). More preferably, it is a medium size alkyl having 1 to 10 carbon atoms. Most preferably, it is a lower alkyl having 1 to 4 carbon atoms. The alkyl group may be substituted or unsubstituted. For example, the term "$C_{1-6}$ alkyl" as used herein and in the claims (unless otherwise specified) mean straight or branched chain alkyl groups such as methyl, ethyl, propyl, isopropyl, butyl, isobutyl, t-butyl, amyl, hexyl and the like.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted.

The present invention comprises compounds of Formula I, their pharmaceutical formulations, and their use in treating or preventing diseases and disorders responsive to the activation of the melanocortin receptors in mammals. General procedures used to construct compounds of Formula I and intermediates useful for their synthesis are described in the following schemes.

Abbreviations

The following abbreviations, most of which are conventional abbreviations well known to those skilled in the art, are used throughout the description of the invention and the examples. Some of the abbreviations used are as follows:

| | |
|---|---|
| h = | hour(s) |
| rt = | room temperature |
| mol = | mole(s) |
| mmol = | millimole(s) |
| g = | gram(s) |
| mg = | milligram(s) |
| mL = | milliliter(s) |
| BOP = | Benzotriazol-1-yloxy-tris(dimethylamino)phosphonium hexafluorophosphate |
| $CDCl_3$ = | Deuterochloroform |
| $CD_3OD$ = | Deuteromethanol |
| $CHCl_3$ = | Chloroform |
| $CH_2Cl_2$ = | Dichloromethane |
| DCC = | Dicyclohexyl carbodiimide |
| DIAD = | Diisopropyl azodicarboxylate |
| DMAP = | 4-Dimethylaminopyridine |
| EDC = | 1-(3-Dimethylaminopropyl)-3-ethylcarbodiimide |
| DMSO = | Dimethylsulfoxide |
| $Et_3N$ = | Triethylamine |
| EtOAc = | Ethyl acetate |
| HCl = | Hydrochloric acid |
| HOBT = | 1-Hydroxy benzotriazole |
| MeOH = | Methanol |
| $NaBH_3CN$ = | Sodium cyanoborohydride |
| NaH = | Sodium hydride |
| NaOH = | Sodium hydroxide |
| $Na_2SO_4$ = | Sodium sulfate |
| $NH_3$ = | Ammonia |
| THF = | Tetrahydrofuran |
| TLC = | Thin layer chromatography |
| $ZnCl_2$ = | Zinc chloride |

Preparation of Intermediates

Reaction Schemes 1–4 depict the synthesis of various intermediates useful for the synthesis of compounds of Formula I. Reaction Scheme 1 depicts the formation of an amide linked piperazine (n=1) or homopiperazine (n=2) intermediate of Formula III, by displacement of a leaving group (L) from the compound of Formula II. The reaction is typically carried out in an aprotic solvent such as dichloromethane and a useful leaving group (L) is the 4-nitrophenoxide group.

Reaction Scheme 1

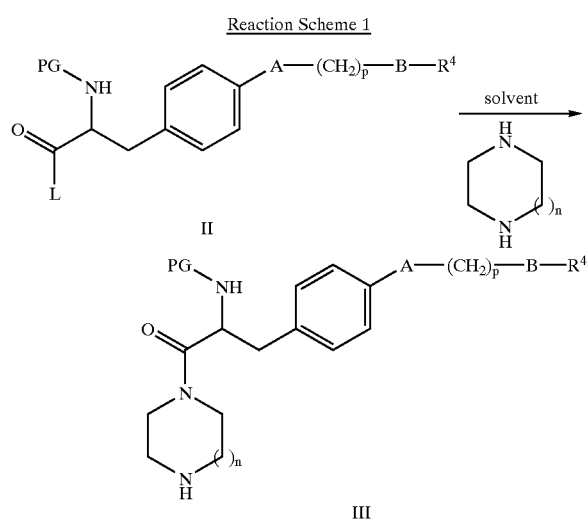

The reaction may be run in the presence of a tertiary amine base, such as triethylamine, diisopropyl ethylamine or 4-methylmorpholine, or an excess of piperazine or homopiperazine may be used. The amine group in both Formulas II and III is protected by a suitable amine protecting group (PG). Amine protecting groups and methods for their removal are well known to those skilled in the art and can be found in Greene, T. and Wuts, P. G. M., *Protective Groups in Organic Synthesis*, John Wiley & Sons, Inc., New York, N.Y. (1991). The tert-butyloxycarbonyl (BOC) group is a common amine protecting group (PG) useful in the synthesis of the compounds of Formula III.

Reaction Scheme 2 depicts the preparation of of piperazine (n=1) or homopiperazine (n=2) intermediates by Lewis acid catalyzed reductive amination. A suitably protected amine of Formula IV is reacted with an appropriate aldehyde ($R^{3'}$CHO) or ketone ($R^{3'}$C(O)$R^{3''}$) in the presence of a Lewis acid and a reducing agent in an appropriate solvent to provide the alkylated intermediate of Formula V. The reaction can be efficiently carried out in a protic solvent such as methanol in the presence of zinc chloride and sodium cyanoborohydride.

Reaction Scheme 2

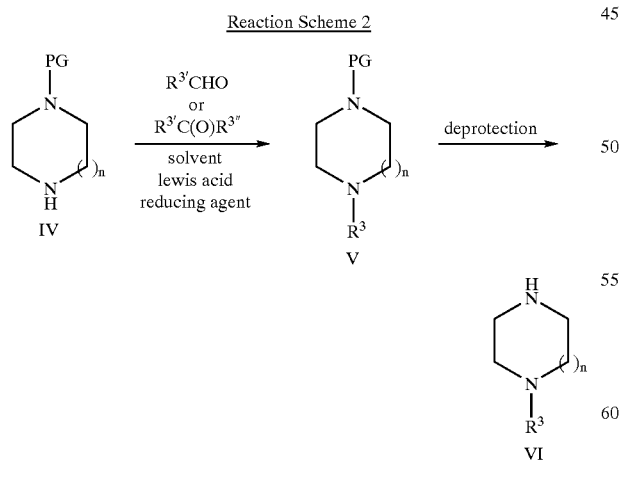

The protecting group on the amine intermediate of Formula V can then be removed by standard methods known in the art to provide intermediate of Formula VI. For example, when PG is carbobenzyloxy (CBZ) it can be removed by catalytic hydrogenation over a suitable catalyst, such as palladium on charcoal, in a protic solvent such as ethanol. Removal of a tert-butyloxycarbonyl (BOC) group is carried out by treatment with a strong acid such as trifluoroacetic acid, hydrochloric acid or hydrogen chloride gas in a solvent such as dichloromethane, dioxane, ethyl acetate or methanol.

Reaction Scheme 3 depicts the preparation of an intermediate of Formula VIII by displacement of the leaving group (L) on intermediate of Formula VII, with an amine of Formula VI. The reaction may be carried out in an aprotic solvent such as dichloromethane in the presence of a tertiary amine base such as diisopropyl ethylamine. For this transformation, a useful leaving group (L) is the 4-nitrophenoxide group.

Reaction Scheme 3

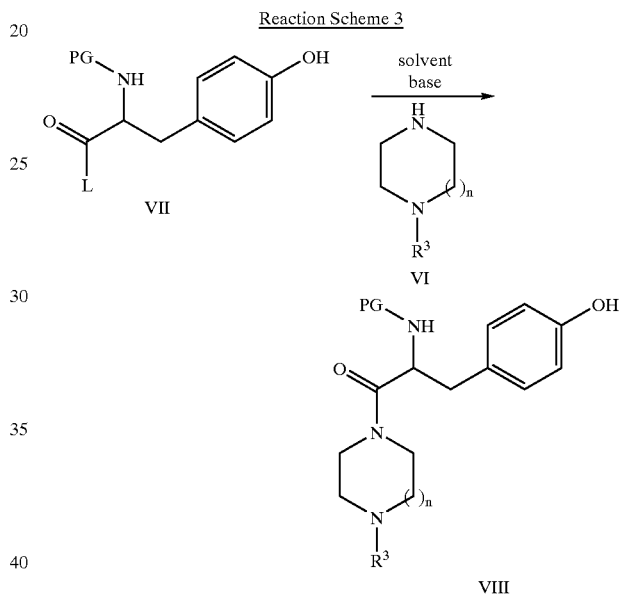

Reaction Scheme 4 shows the preparation of the iodide intermediate of Formula X by using standard peptide coupling methods to couple the acid of Formula IX and the amine of Formula VI. The term "standard peptide coupling" as used herein means coupling a carboxylic acid with an amine using an acid activating agent such as EDC, DCC or BOP in an inert solvent such as dichloromethane. A tertiary amine base, such as triethylamine, diisopropyl ethylamine, or 4-methylmorpholine may be required in some instances, and a catalyst such as HOBT may also be used.

Reaction Scheme 4

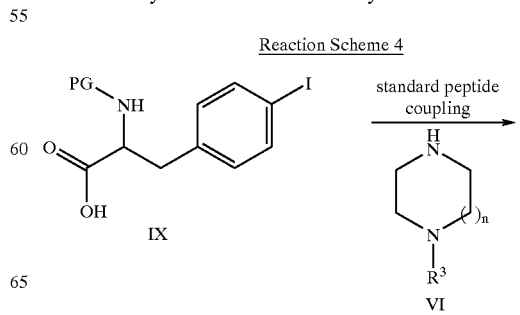

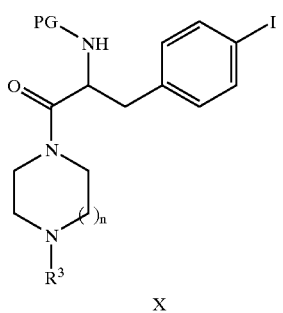

X

Preparation of Compounds of Formula I

Reaction Scheme 5 depicts the synthesis of compounds of Formula I by a Lewis acid catalyzed reductive amination method. A suitably protected intermediate of Formula III is reacted with an appropriate aldehyde ($R^{3'}$CHO) or ketone ($R^{3'}$C(O)$R^{3''}$) in the presence of a Lewis acid and a reducing agent in an appropriate solvent to provide the alkylated intermediate of Formula XI. The reaction can be efficiently carried out in a protic solvent such as methanol in the presence of zinc chloride and sodium cyanoborohydride. The amine protecting group of intermediate of Formula XI is then removed by standard methods such as described previously in Reaction Scheme 2 to provide compounds of Formula I.

Reaction Scheme 6 depicts the preparation of compounds of Formula I wherein the amino group ox to the amide carbonyl has been monoalkylated. The acid intermediate of Formula XII and the amine of Formula VI are coupled using standard peptide coupling methods (as previously described for Reaction Scheme 4) to provide intermediate of Formula XI. The intermediate of Formula XI is then deprotected using standard methods known to those skilled in the art to provide a compound of Formula I wherein $R^1$ and $R^2$ are hydrogen. This intermediate is then reacted with 2,4-dinitrobenzenesulfonyl chloride in the presence of a tertiary amine base, such as triethylamine, in an appropriate solvent, such as dichloromethane, to provide intermediate of Formula XIII. The intermediate of Formula XIII may then be alkylated with alkyl halides or by Mitsunobu reactions with various alcohols according to the methods described by Fukuyama, T., et al. in *Tetrahedron Lett.* (1997) 5831–5834. For example, reaction of intermediate of Formula XIII with an appropriate alcohol of formula $R^1$OH in the presence of triphenylphosphine and DIAD in an appropriate solvent, such as anhydrous dichloromethane, results in the alkylated sulfonamide intermediate of Formula XIV. The 2,4-dinitrobenzenesulfonyl moiety may then be removed by treatment of the reaction mixture with an excess of a tertiary amine base, such as triethylamine, and an excess of mercaptoacetic acid to provide the monoalkylated compound of Formula I.

Reaction Scheme 5

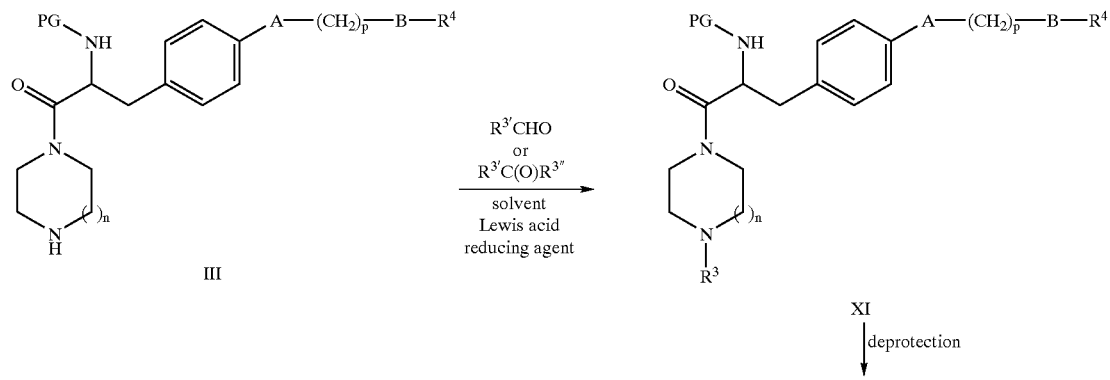

III

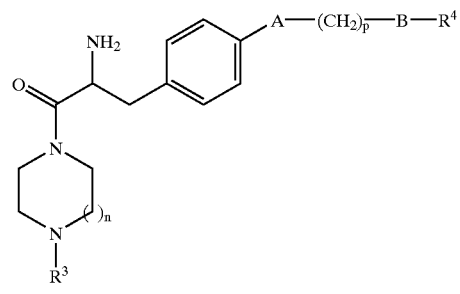

I

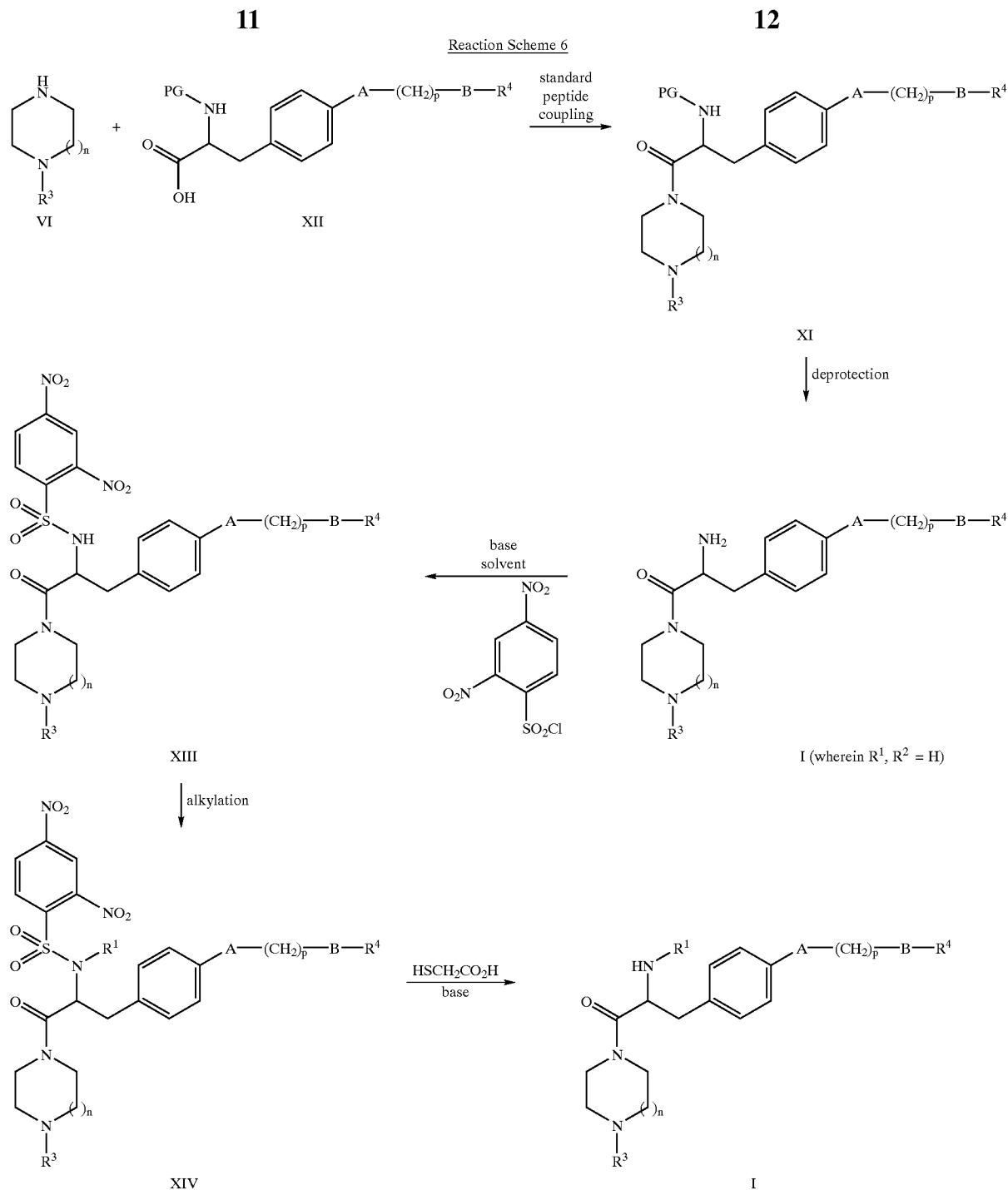

Reaction Scheme 6

It is to be understood by one skilled in the art that other methods of alkylation can also be used to prepare compounds of Formula I. For example, intermediate of Formula XI in Reaction Scheme 6 (wherein PG is tert-butyloxycarbonyl) may be alkylated upon treatment with a metal hydride base, such as sodium hydride, and an alkyl halide, such as methyl iodide, in an appropriate solvent, such as tetrahydrofuran. The tert-butyloxycarbonyl group may then be removed under standard conditions to provide monoalkylated compounds of Formula I. Alternatively, a compound of Formula I which contains a primary or secondary amine group can be alkylated by reductive amination methods as previously described for Reaction Scheme 5.

Reaction Scheme 7, as illustrated below, depicts the preparation of compounds of Formula I by Mitsunobu alkylation of the phenolic hydroxyl group. Intermediate of Formula VIIIa is first prepared by displacement of the 4-nitrophenoxide moiety of intermediate of Formula XV with an appropriate amine of Formula VI in the presence of a tertiary amine base, such as triethylamine, in an aprotic solvent such as dichloromethane. Intermediate of Formula VIIIa is then O-alkylated under typical Mitsunobu reaction conditions (triphenylphosphine, DIAD, in dichloromethane) with an appropriate alcohol, $HO(CH_2)_pBR^4$ to provide an intermediate of Formula XVI. The amine protecting group (PG) can then be removed by standard methods described previously for Reaction Scheme 2 to provide compounds of Formula I. The amine group which was deprotected can then be further alkylated, if desired, using the methods previously described for Reaction Scheme 6.

Reaction Scheme 7

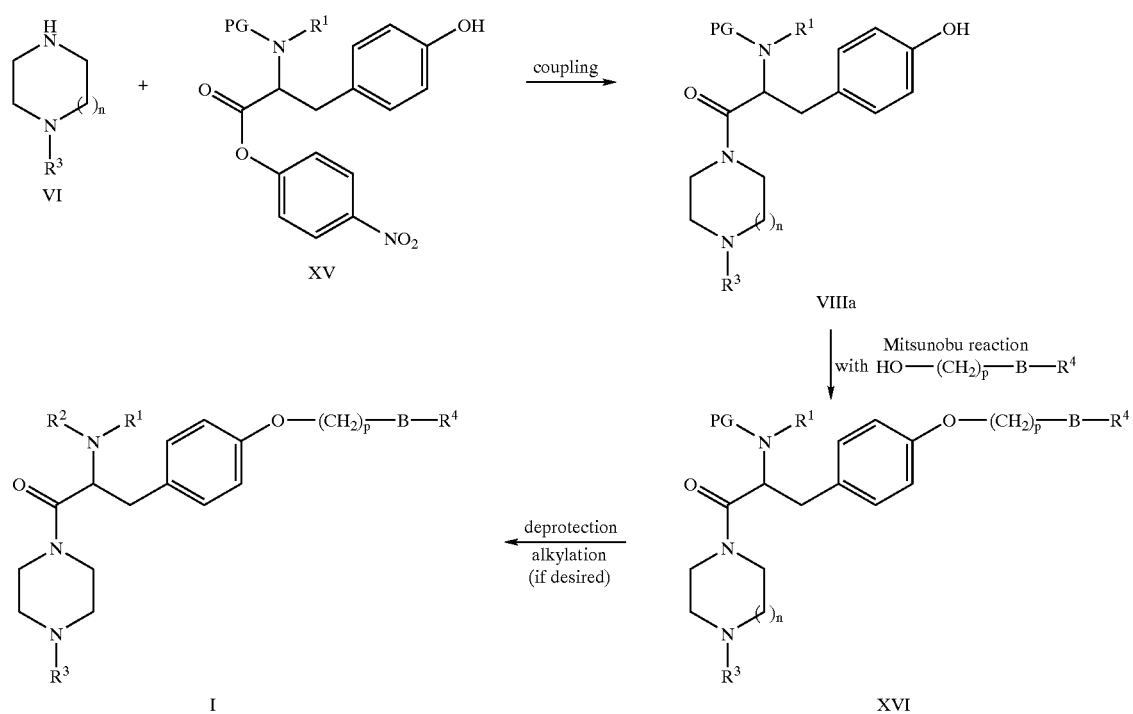

Reaction Scheme 8 depicts the preparation of compounds of Formula Ia using Suzuki coupling of an aryl iodide to an aryl boronic acid or heteroaryl boronic acid ($R^4$ is aryl or heteroaryl). Intermediate of Formula X is treated with an appropriate aryl boronic acid or heteroaryl boronic acid, $R^4B(OH)_2$ in the presence of an appropriate palladium catalyst, such as tetrakis triphenylphosphine palladium, and a base, such as sodium carbonate, in a solvent, such as ethanol, to provide intermediate of Formula XVII. The intermediate of Formula XVII is then subjected to the standard conditions, as described for Reaction Scheme 2 to remove the amine protecting group (PG) and provide a compound of Formula Ia.

Reaction Scheme 8

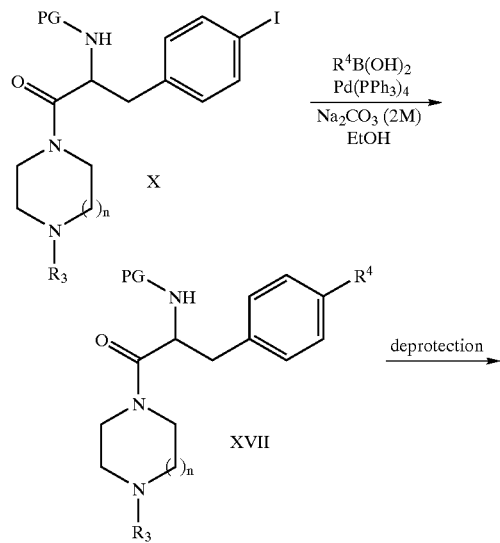

Reaction Scheme 9 shows the preparation of compounds of Formula Ib using modified Ullman coupling conditions. The compound of Formula XIII is reacted with phenyl boronic acid or a substituted phenyl boronic acid ($R^4B(OH)_2$) in the presence of copper (II) acetate, molecular sieves, a base, such as pyridine, and an aprotic solvent such as dichloromethane. The intermediate of Formula XVIII can then be deprotected using standard methods to provide the biaryl ether derivative of Formula Ib.

Reaction Scheme 9

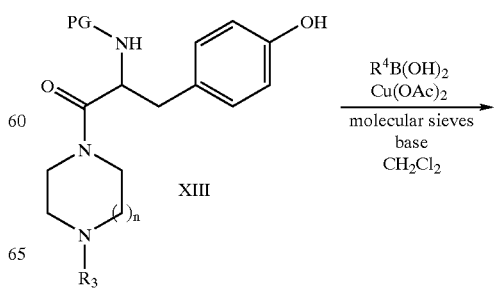

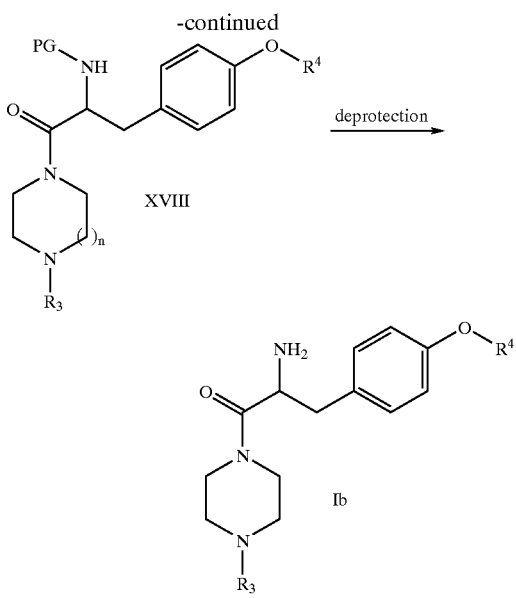

In a preferred embodiment, the present invention provides compounds of Formula I, or a pharmaceutically acceptable salt thereof, wherein the stereochemistry of the chiral carbon marked by the * has the S configuration.

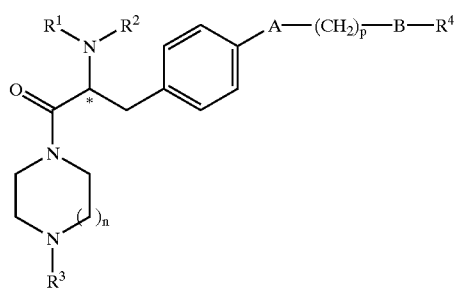

In another preferred embodiment, the present invention provides compounds of Formula I, or a pharmaceutically acceptable salt thereof, wherein
$R^3$ is

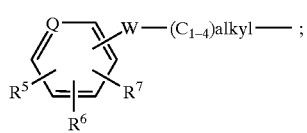

and
Q is $CR^8$

In still another preferred embodiment, the present invention provides compounds of Formula I, or a pharmaceutically acceptable salt thereof, wherein A is O; and
$R^4$ is phenyl; wherein said phenyl is optionally substituted with one to three substituents each independently selected from halogen, trifluoromethyl, trifluoromethoxy, nitro, $C_{1-4}$alkyl, $C_{1-4}$alkoxy, $C_{1-4}$ thioalkoxy, $C_{1-4}$alkylcarbonyl, di($C_{1-4}$alkyl)amino, amino, carboxyl, phenyl, phenyl($C_{1-4}$) alkyl, phenyloxy, and phenylmethoxy.

In yet another preferred embodiment, the present invention provides compounds of Formula I, or a pharmaceutically acceptable salt thereof, wherein
is O;
A and B taken together are a bond; and
$R^4$ is selected from the group consisting of phenyl, napthalenyl, benzodioxolyl, benzodioxanyl, pyridinyl, quinolinyl, thienyl, benzothienyl, dibenzothienyl, and phenoxathiinyl; and wherein said phenyl, thienyl and pyridyl are optionally substituted with one to three substituents each independently selected from halogen, trifluoromethyl, trifluoromethoxy, nitro, $C_{1-4}$alkyl, $C_{1-4}$alkoxy, $C_{1-4}$thioalkoxy, $C_{1-4}$alkylcarbonyl, di($C_{1-4}$ alkyl)amino, amino, carboxyl, phenyl, phenyl($C_{1-4}$)alkyl, phenyloxy, and phenylmethoxy.

In another aspect, the present invention provides pharmaceutical compositions comprising at least one compound of Formula I in combination with a pharmaceutically acceptable carrier, adjuvant or diluent.

In a further aspect, the present invention provides pharmaceutical compositions further comprising a second active ingredient selected from the group consisting of a sequestrant cholesterol lowering agent, neuropeptide Y antagonist, and an α-2 adrenergic receptor antagonist in combination with a pharmaceutically acceptable carrier, adjuvant or diluent.

In still another aspect, the present invention provides a method for the treatment or prevention of disorders, diseases or conditions responsive to the activation of melanocortin receptor(s) which comprises administering to a mammal in need of such treatment or prevention a therapeutically effective amount of a compound as described in claim 1 or any of the preferred embodiments of the present invention. Preferably, the compounds of Formula I are useful in the treatment or prevention of obesity, diabetes, sexual dysfunction and other disorders responsive to the activation of melanocortin receptor(s).

Biological Assays
A. Binding Assay

The membrane binding assay is used to identify competitive inhibitors of [$^{125}$I]NDP-α-MSH binding to cloned human MC4R expressed in Hi5 insect cells infected by a baculovirus/human MC4R receptor construct.

Hi5 cells are grown in suspension in Express Five SFM Insect Cell Media (Gibco, Cat. No. 10486-025) at 27° C. with constant shaking. Hi5 cells are infected using the following protocol:

Cells at a density of 1×10$^6$ cells/mL are spun down at 1000 rpm (Beckman GS-6KR centrifuge) for 10 minutes.

Cells are resuspended in 10% of their original volume in a sterile 50 mL conical centrifuge tube wrapped with aluminum foil. Virus is added at a Multiplicity of Infection (MOI) of 3 and incubated for 1 hour at room temperature with gentle shaking.

This cell/virus mix is added to the appropriate volume of medium to attain the original volume and incubated at 27° C. with constant shaking for 72 hours.

Cells are spun down in 50 mL conical centrifuge tubes at 1000 rpm for 10 minutes. Each of the resulting pellets are resuspended in 10 mL of cold (4° C.) membrane buffer (25 mM HEPES, pH 7.4, 140 mM NaCl, 1.2 mM MgCl$_2$, 2.5 mM CaCl$_2$, 10 μG/mL Aprotinin, 10 μG/mL Leupeptin) and Dounce homogenized using 10–12 strokes. Dilute to 30 mL with buffer and centrifuge at 18,000 rpm, 4° C., 15 minutes (Sorvall RC5C Centrifuge). The resulting pellet is resuspended in cold membrane buffer in a total of ¼ of the original volume by vortexing and aspiration using a syringe and 27 gauge needle.

Protein content is determined (Bradford, Bio-Rad Protein Assay). Membranes are aliquoted in microcentrifuge tubes and quick frozen in liquid nitrogen. Store at −80° C. until use.

The membrane binding buffer is composed of 25 mM HEPES, pH 7.4, 140 mM NaCl, 1.2 mM $MgCl_2$, 2.5 mM $CaCl_2$, 0.1% BSA. 160 μL of membrane binding buffer containing 0.5 μg membrane protein is added to 20 μL of 1.0 nM [$^{125}$I]-NDP-α-MSH (final concentration is 0.1 nM) and 20 μL of competing drug or buffer and incubated for 90 minutes at 37° C.

The mixture is filtered with Brandel Microplate 96 filter apparatus using 96-well GF/B filter presoaked in 1-% polyethyleneimine (Sigma). The filter is washed (4 times with a total of 1 mL per well) with cold wash buffer consisting of 20 mM HEPES, pH 7.4, 5 mM $MgCl_2$.

The filter is dried and punched into a 96 well sample plate (Wallac, 1450-401). 100 μl of Wallac Optiphase Supermix scintillation fluid is added to each well. The top is sealed and the plates are shaken to insure that the filters are thoroughly soaked with fluid. Plates are then counted in a Wallac Microbeta Trilux Scintillation and Luminescence Counter (Model 1450). Dose-response curves are fitted by linear regression analyses and $IC_{50}$ values are calculated using ExcelFit.

B. Functional Assay

Functional membrane based [$^{35}$S]GTPγS binding assays are developed to discriminate agonists and antagonists.

Membrane preparation. Cells (HEK-293 cells expressing the human MC4R) are grown in Minimum Essential Medium with Earle's salts and L-glutamate (Life Technologies, Cat. # 11095-080) containing 10% heat-inactivated fetal bovine serum, 400 μg/mL geneticin and 100 mM sodium pyruvate in T175 flasks. Upon reaching confluence, cells are dissociated from tissue culture flasks by rinsing with $Ca^{2+}$ and $Mg^{2+}$ free phosphate buffered saline (Life Technologies, Cat. # 14190-144) and detached following 5 minutes incubation at 37° C. with enzyme free cell dissociation buffer (Life Technologies, Cat. # 13151-014). Cells are collected by centrifugation and resuspended in membrane preparation buffer consisting of 20 mM HEPES, pH 7.4, 10 mM EDTA, 10 μg/mL aprotinin and 10 μg/mL leupeptin. The suspension is homogenized by polytron PT3000 for 30 sec at 20,000 rpm, and centrifuged at 35,000×g for 15 minutes at 4° C. The pellet is resuspended in membrane preparation buffer and the last centrifugation is repeated. The final pellet is resuspended in membrane storage buffer consisting of 20 mM HEPES, pH 7.4, 0.1 mM EDTA, 10 μg/mL aprotinin and 10 μg/mL leupeptin. Protein concentration is determined by the Bio-Rad method (Bio-Rad, Cat.# 500-0006) and the preparation is diluted to a final protein concentration of 1 mg/mL. Aliquots are stored at −70° C. until used.

[$^{35}$S]GTPγS membrane binding assay. Compounds are dissolved at 10 mM concentration in DMSO and diluted to the requited concentration into assay buffer. GTPγS to determine nonspecific binding is prepared at 100 μM concentration in assay buffer. The final concentration of DMSO in the assay is 1%. The assay buffer is consisting of 20 mM HEPES, pH 7.4, 100 mM NaCl, 5 mM $MgCl_2$, 0.5 μM GDP, 10 μg/mL saponin,10 μg/mL aprotinin and 10 μg/mL leupeptin. The assay is composed by adding 50 μL 10×drug solution, 200 μL membrane preparation (containing 2–4 μg protein), 50 μL [$^{35}$S]GTPγS (100,000–150,000 CPM) and 200 μL assay buffer to achieve a total volume of 500 μL. The assay mixture is incubated at room temperature for exactly 30 minutes. The reaction is terminated by rapid filtration under vacuum through Whatman GF/B filters using a Brandel 96 wells cell harvester, followed by washing four times with cold wash buffer consisting of 20 mM HEPES, pH 7.4, and 5 mM $MgCl_2$. The filters are air-dried and 200 μL Wallac, Optiphase Super Mix, liquid scintillation cocktail is added to each filter. The bound radioactivity (CPM) is determined by Wallac Trilux 1450 MicroBeta liquid scintillation and Luminescence counter after six hours.

Data interpretation. NDP-α-MSH is used as reference compound and its maximal stimulation is measured at 1 μM (Ref CPM 100%). Total drug-independent binding (Total CPM) is measured in the absence of compounds. Response triggered by compounds is expressed as percent NDP-α-MSH response. Compound dose response curves are generated by Excel XL Fit. The top of the curve represents the compound's intrinsic activity expressed as % of maximal stimulation.

In vivo Food Intake Models

1) Overnight food intake. Sprague Dawley rats are injected intracerebrovenrricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 hours post compound administration is measured.

2) Food intake in diet induced obese mice. Male C57IB16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food arid water ad lib and are kept on a normal light/dark cycle. Studies are conducted during the light cycle.

a) Conditioning to Supine Restraint for Ex Copula Reflex Tests. This conditioning takes 4 days. Day 1, the animals are placed in a darkened restrainer and left for 15–30 minutes. Day 2, the animals are restrained in a supine position in the restrainer for 15–30 minutes. Day 3, the animals are restrained in thesupine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

b) Ex Copula Reflex Tests. Rats are gently restrained in a supine position with their anterior torso placed inside a cylinder of adequate size to allow for normal head and paw grooming. For a 400–500 gram rat, the diameter of the cylinder is approximately g cm. The lower torso and hind limbs are restrained with a non adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement. cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability. Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfimetion are described in McKenna K B et al., A Model 15 *For The Study Of Sexual Function In Anesthetized Male And Female Rats*, Am. J. Physiol. (Regulatory Integrative Comp. Physiol 30): R1276–R1284, 1991; McKenna K B et al., *Modulation By Peripheral Serotonin Of The Threshold For Sexual Reflexes In Female Rats*, Pharm. Bioch. Behav., 40:151–156, 1991; and Takahashi L K et al., *Dual Estradiol Action In The Diencephalon And The Regulation Of Sociosexual 20 Behavior In Female Golden Hamsters*, Brain Res., 359:194–207, 1985.

Administration, Dose Ranges and Pharmaceutical Compositions

On the basis of pharmacologic testing, an effective dose given parenterally could be expected to be in a range of about 0.05 to 1 mg/kg body weight and if given orally would be expected to be in the range of about 1 to 20 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, buccal, transdermal, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anoretic effects without causing any harmful or untoward side effects. Similarly, the instant compounds can be administered to treat hypertension, depression, diabetes and anxiety disorders.

Therapeutically, the instant compounds are generally given as pharmaceutical compositions comprised of an effective anorectic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the pre-determined dosage regimen usually a whole, half, third, or quarter of the daily dosage administered once, twice, three, or four times a day. Other therapeutic agents can also be present. Pharmaceutical compositions which provide from about 50 to 1000 mg of the active ingredient per unit dose are preferred and are conventionally prepared as tablets, lozenges, capsules, powders, transdermal patches, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are generally employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyethelene glycols or mixtures thereof. The polyethyleneglycols consist of a mixture of non-volatile, usually liquid, polyethyleneglycols which are soluble in both water and organic liquids and which have molecular weights from about 200 to 1500.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula 1, either administered separately or in the same pharmaceutical compositions', include, but are not limited to:

(a) insulin sensitizers including (i) PPARy agonists such as the glitazones (e.g. troglitazone, pioglitazone, englitazone, MCC-555. BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide;

(d) α-glucosidase inhibitors (such as acarbose), (e) cholesterol lowering agents such as (i) HMG-CoA reductase inhibitors (lovastatin, simvastatin and pravastatin, fluvastatin. atorvastatin, and other statins), (ii) sequestrants (cholestyramine, colestipol arid a dialkylaminoalkyl derivatives of a cross-linked dextran), (ii) nicotinyl alcohol nicotinic acid or a salt thereof, (iii) proliferator-activater receptor a agonists such as fenofibric acid derivatives (gemlibrozil, clofibrat, fenofibrate and benzafibrate), (iv) inhibitors of cholesterol absorption for example beta-sitosterol arid (acyl CoA:cholesterol acyltransferase) inhibitors for example melinamide, (v) probucol, (vi) vitamin E, and (vii) thyromimetics;

(f) PPARδ agonists such as those disclosed in WO97/28149;

(g) antiobesity compounds such as fenfluramie, dexfenfluramine, phentermine, sibutramine, orlistat, or $\beta_3$ adrenergic receptor agonists;

(h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(i) PPARα agonists such as described in WO 97/36579 by Glaxo;

(j) PPARγ antagonists as described in WO97/10813;

(k) serotonin reuptake inhibitors such as fluoxetine and sertraline;

(l) growth hormone secretagogues such as MK-0677; and (m) agents useful in the treatment of male and/or female sexual dysfunction such as phosphodiester V inhibitors such as sildenafil, and α-2 adrenergic receptor antagonists.

DESCRIPTION OF SPECIFIC EMBODIMENTS

General Methods. All the representative compounds displayed spectral characteristics (MS, $^1$H and $^{13}$C NMR) which were consistent with their assigned structures. Library compounds were generally assigned by the known reaction sequences and characterized by HPLC, LCMS and LRMS. $^1$H and $^{13}$C NMR's were run in the indicated soivent [deuterochloroform (CDCl$_3$), perdeuterodimethylsulfoxide (DMSO-d$_6$) or perdeuteromethanol (CD$_3$OD)] at 300 MHz using a Bruker ACP 300 spectrometer. Data are reported as follows: chemical shift (δ) in PPM downfield from calculated tetramethylsilane (TMS); multiplicity (s=singlet, d=doublet, t=triplet, q=quartet, p=pentuplet, and br=broadened), coupling constant (given in Hz) and integration. Unless otherwise indicated, all starting materials such as N-(tert-butyloxycarbonyl)-O-benzyltyrosine and the 4-nitrophenol ester thereof, piperizine, homopiperizine, all aldehydes and ketones etc. used in the synthesis of compounds of Formula I were available from commercial sources.

Preparation of Intermediates

Intermediate 1

N-(tert-Butyloxycarbonyl)-O-(phenylmethyl)-L-tyrosine, 1-homopiperazine amide

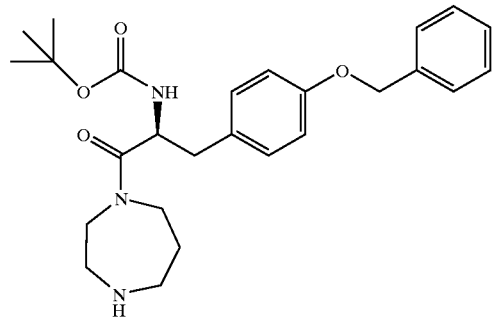

To a solution of N-(tert-butyloxycarbonyl)-O-(phenylmethyl)-L-tyrosine, 4-nitrophenol ester (1.0 equiv.) dissolved in CH$_2$Cl$_2$ (0.15 M) was added homopiperazine (3.0 equiv.) in one portion at room temperature. The yellow reaction mixture was stirred at room temperature for 2 hours and the starting ester was completely consumed by monitoring with TLC. The reaction mixture was then washed with 1N NaOH and water to afford a colorless solution. The CH$_2$Cl$_2$ solution was then dried over Na$_2$SO$_4$, filtered and the filtrate was concentrated in vacuo to afford a colorless foam in quantitative yield. The title compound was pure enough to carry on to the next reaction without further purification: IR (KBr) v3299, 2932, 1703, 1634, 1510, 1243, 1171, 1019, 737 cm$^{-1}$; $^1$H NMR (CDCl$_3$) δ7.46–7.28 (m, 5H), 7.12 (d, J=8.6 Hz, 2H), 6.89 (d, J=8.6 Hz, 2H), 5.34–5.29 (m, 1H), 5.05 (s, 2H), 4.80–4.60 (m, 1H), 3.80–1.50 (m, 13H), 1.42 (s, 9H); $^{13}$C NMR (CDCl$_3$) δ171.9, 158.0, 155.4, 137.2, 130.8, 129.0, 128.8, 128.1, 127.7, 115.1, 80.1, 70.2, 51.8, 49.5, 48.2, 47.8, 46.9, 45.4, 39.4, 28.5; MS Calcd for [C$_{26}$H$_{35}$N$_3$O$_4$+H]$^+$: 454. Found: 454.

---

Anal. Calcd for C$_{26}$H$_{35}$N$_3$O$_4$ · (0.06)CH$_2$Cl$_2$: C, 66.18; H, 7.56; N, 8.71.
Found: C, 66.23; H, 7.75; N, 8.83.

Intermediate 2

N-(tert-Butyloxycarbonyl)-O-(phenylmethyl)-L-tyrosine, 1-piperazine amide

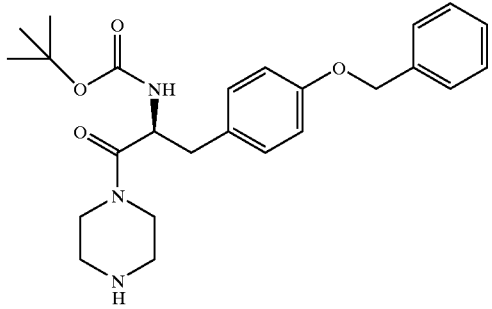

The title compound was synthesized following the same procedure as described for the synthesis of intermediate (1) starting from N-(tert-butyloxycarbonyl)-O-(phenylmethyl)-L-tyrosine, 4-nitrophenol ester (1.0 equiv.) dissolved in $CH_2Cl_2$ (0.15 M) and piperazine (3.0 equiv.). $^1H$ NMR ($CDCl_3$) δ 7.44–7.32 (m 5H), 7.10 (d, J=8.6 Hz, 2H), 6.90 (d, J=8.6 Hz, 2H), 5.40 (br, 1H), 5.06 (s, 2H), 4.78 (m, 1H), 3.60–2.10 (m, 11H), 1.43 (s, 9H).

Intermediate 3

N-[(tert-Butyloxycarbonyl]-N'-(2,3-dichlorobenzyl)piperazine

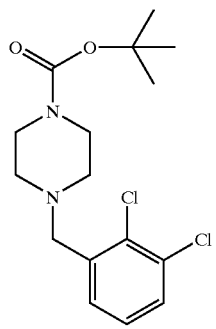

To a solution of N-(tert-butyloxycarbonyl)piperazine (8.73 g, 47 mmol, 1.0 equiv.) and 2,3-dichlorobenzylaldehyde (8.26 g, 48 mmol, 1.01 equiv.) in MeOH (200 mL) at room temperature was added $ZnCl_2$ (6.37 g, 47 mmol, 1.0 equiv.) in one portion followed, after 5 minutes stirring, by $NaBH_3CN$ (2.96 g, 47 mmol, 1.0 equiv.) in portions. The reaction was allowed to stir overnight (16 hours). The reaction mixture was concentrated in vacuo and diluted in $CH_2Cl_2$. The organic layer was washed with 1N NaOH twice and water twice, dried over $Na_2SO_4$, and concentrated. Purification by flash column chromatography on silica (EtOAc/hexane from 1:9 to 1:5) afforded the titled product (8.25 g, 51%) as a colorless oil: $^1H$ NMR ($CDCl_3$) δ 7.42–7.16 (m, 3H), 3.65 (s, 2H), 3.45 (br, 4H), 2.47 (br, 4H), 1.47 (s, 9H).

Intermediate 4

N-(2,3-Dichlorophenylmethyl)piperazine, dihydrochloride salt

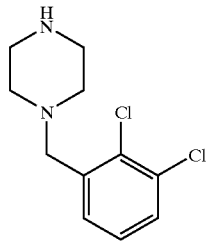

To a solution of N-[(tert-butyloxycarbonyl]-N'-(2,3-dichlorobenzyl)piperazine [Intermediate 3, (8.25 g, 24 mmol)] in MeOH (200 mL) was added concentrated aqueous HCl solution (15 mL) slowly in portions. The reaction was stirred overnight and the first crop of product crystallized out. The reaction mixture was filtered and the filter cake was rinsed with $Et_2O$ to afford a white crystalline solid (4.1 g). The filtrate was concentrated to about ⅓ of the original volume and a second crop of crystalline product was collected by filtration (2.9 g). The combined yield of the title product was 92%. $^1H$ NMR (DMSO-$d_6$) δ 9.81 (br, 2H), 7.87 (d, J=7.5 Hz, 1H), 7.75 (d, J=8.0 Hz), 7.47 (t, J=7.9 Hz), 4.45 (s, 2H), 3.40 (s, 4H), 3.16 (s, 1H); $^{13}C$ NMR (DMSO-$d_6$) δ 133.0, 132.6, 132.5, 131.9, 128.7, 56.9, 48.2, 40.6; MS Calcd for $[C_{11}H_{14}Cl_2N_2+H]^+$: 245. found: 245.

Anal Calcd for $C_{11}H_{14}Cl_2N_2 \cdot 2HCl$: C, 41.54; H, 5.07; N, 8.81. Found: C, 41.29; H, 5.34; N, 8.47.

Intermediate 5

N-(tert-Butyloxycarbonyl)-L-tyrosine, 1-[4-[(2,3-dichlorophenyl)methyl)]piperazine]amide

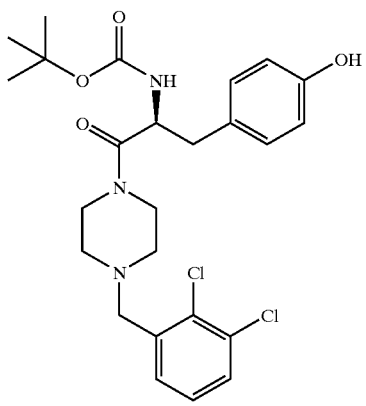

To a solution of N-[(2,3-dichlorophenyl)methyl]piperazine, dihydrochloride salt [Intermediate (4), (1.47 g, 4.6 mmol)] and diisopropyl ethylamine (2.10 g, 16.2 mmol) in CH$_2$Cl$_2$ (40 mL) was added N-(tert-butyloxycarbonyl)-L-tyrosine, 4-nitrophenol ester (1.86 g, 4.6 mmol, 1.0 equiv.) in one portion at room temperature. The yellow reaction mixture was stirred at room temperature overnight and was then washed with saturated NaHCO$_3$ (5×40 mL) and H$_2$O (3×40 mL). The organic layer was dried over Na$_2$SO$_4$, filtered and the filtrate concentrated in vacuo to afford the titled product (2.31 g, 99%) as a white solid: HPLC purity: 100%; $^1$H NMR (CDCl$_3$) δ 7.48–7.41 (m, 2H), 7.23 (d, J=7.9 Hz, 1H), 7.01 (d, J=8.3 Hz, 2H), 6.76 (d, J=8.4 Hz, 2H), 5.38 (d, J=8.6 Hz, 1H), 4.71 (q, J=7.7 Hz, 1H), 3.92 (br, 2H), 3.71 (br, 2H), 3.49–3.41 (m, 1H), 3.15 (br, 1H), 2.94 (dd, J=13.2 and 5.3 Hz, 1H), 2.84 (dd, J=13.1 and 9.3 Hz, 1H), 2.80–2.56 (br, 4H), 2.18–2.00 (m, 1H), 1.42 (s, 9H); $^{13}$C NMR (CDCl$_3$) δ 170.77, 155.69, 155.41, 134.02, 133.44, 131.25, 130.88, 130.39, 128.06, 116.07, 80.35, 58.45, 51.97, 51.84, 51.30, 44.05, 40.48, 39.65, 28.57; MS Calcd for [C$_{25}$H$_{31}$Cl$_2$N$_3$O$_4$+H]$^+$: 508. found: 508.

Intermediate 6

[(N-tert-Butyloxycarbonyl)-(3-(4-iodophenyl)-L-alanine)], 1-[4-(2,3-dichlorophenyl)methyl)] piperazine amide

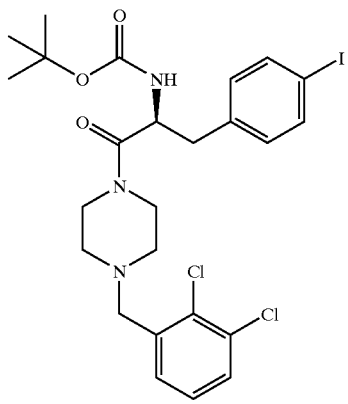

To a solution of N-(tert-butyloxycarbonyl)-3-(4-iodophenyl)alanine (5.09 g, 13 mmol, 1.0 equiv.) in CH$_2$Cl$_2$ (130 mL) at room temperature was added N-(2,3-Dichlorophenylmethyl)piperazine, dihydrochloride salt [Intermediate (4), (4.55 g, 14.3 mmol, 1.1 equiv.)], 1-[3-(dimethylamino)propyl]-3-ethylcarbodiimide hydrochloride (EDC) (4.99 g, 26 mmol, 2.0 equiv.) and Et$_3$N (7.25 mL, 52 mmol, 4.0 equiv.). The resulted mixture was stirred at room temperature overnight (16 hours). The mixture was then diluted with CH$_2$Cl$_2$, washed with water and brine. The organic layer was dried over Na$_2$SO$_4$, filtered and the filtrate concentrated in vacuo. Purification by flash column chromatography on silica (8:1 CH$_2$Cl$_2$/EtOAc) afforded the titled product (3.1 g, 38.5%) as a white solid: $^1$H NMR (CDCl$_3$) δ 7.61 (d, J=8.3 Hz, 2H), 7.39–7.30 (m, 2H), 7.17 (t, J=7.8 Hz, 1H), 6.94 (d, J=8.2 Hz, 2H), 5.38 (d, J=8.5 Hz, 1H), 4.78 (q, j=7.6 Hz, 1H), 3.69–3.16 (m, 6H), 2.90 (d, J=7.2 Hz, 2H 2.47–2.24 (m, 3H), 1.82–1.72 (m, 1H), 1.41 (s, 9H); $^{13}$C NMR (CDCl$_3$) δ 169.83, 155.23, 137.83, 136.36, 133.53, 132.85, 131.91, 129.45, 128.81, 127.24, 92.56, 80.11, 59.99, 52.82, 50.83, 45.85, 42.27, 39.88, 28.56; MS Calcd for [C$_{25}$H$_{30}$Cl$_2$IN$_3$O$_3$+H]$^+$: 618. found: 618.

Preparation of Formula I Compounds

EXAMPLES 1–158

General Procedure for the Synthesis of Examples 1–158 by Reductive Amination and Deprotection Examples 1–158 were prepared by parallel synthesis using either a 48- or 96-well mini-reactor. The starting piperazine or homopiperazine intermediate (Intermediate (1) or (2), above) was dissolved in MeOH and transferred to each well (20 mg, 1 equiv.) by Tecan. Using a Smart-Balance a suitable aldehyde or ketone was added to each well (1.1 equiv.) as a MeOH solution. MeOH solutions of ZnCl$_2$ (1.0 equiv.) and NaBH$_3$CN (1.0 equiv.) were then transferred to each well by Tecan. The mini-reactor was put on a shaker and shaken for 12 hours. MeOH was removed by concentating in vacuo using a Speed Vac and the residue was suspended in CH$_2$Cl$_2$. The CH$_2$Cl$_2$ suspension was then subjected to a cotton filtration in order to remove inorganic solids. The resulting filtrate was applied to an SCX cartridge which was then rinsed with CH$_2$Cl$_2$ and MeOH in order to remove the excess aldehyde or ketone. The SCX cartridge was then eluted with NH$_3$/MeOH (2 M), and intermediate and partially deprotected product was eluted from the cartridge. Most reactions were essentially pure (two peaks). Impure reactions were purified by preparative HPLC. The intermediates/partially deprotected products were again transferred back into 48- or 96-well mini-reactor with 1 mL MeOH each. 1 mL of HCl/dioxane (4 M) was added to each well, and the reactor shaken for 2 hours. Evaporation by Speed Vac afforded pure products as analyzed by LC/MS (impure products were again purified by preparative HPLC) and HPLC to afford the products (Examples 1–158) shown in Tables 1 and 2, below. The observed molecular mass (M+H)$^+$, and biological activity for Examples 1–158 are also provided in Tables 1 and 2.

The following displacement and IC$_{50}$ (μM) rates apply to Tables 1 through 11.

| Displacement Rate (%) (at 10 μM) | MC4R IC$_{50}$ (μM) |
|---|---|
| +++ = 91–100 | A = <1.5 |
| ++ = 71–90 | B = 1.5–3.0 |
| + = 35–70 | C = >3.0 |

TABLE 1

| Example No. | R³ | MS (M + H)⁺ | Displacement Rate (%) (at 10 μM) | MC4R IC$_{50}$ (μM) |
|---|---|---|---|---|
| 1 | (4-benzhydrylphenyl)methyl | 611 | +++ | A |
| 2 | [2-(4-chlorophenylthio)phenyl]methyl | 586 | +++ | B |
| 3 | (9-ethylcarbazol-3-yl)methyl | 561 | +++ | A |
| 4 | [3-(3,5-dichlorophenoxy)phenyl]methyl | 604 | +++ | A |
| 5 | [3-(benzyloxy)phenyl]methyl | 549 | +++ | B |
| 6 | [5-(4-chlorophenyl)furan-2-yl]methyl | 544 | +++ | B |

TABLE 1-continued
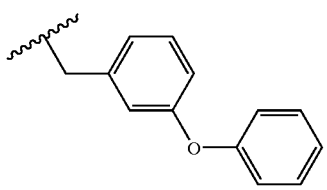
| Example No. | R³ | MS (M + H)⁺ | Displacement Rate (%) (at 10 μM) | MC4R IC$_{50}$ (μM) |
| --- | --- | --- | --- | --- |
| 7 | 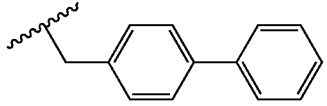 | 535 | +++ | A |
| 8 | 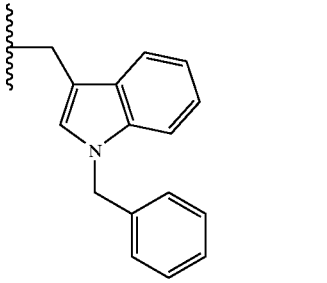 | 520 | +++ | B |
| 9 | 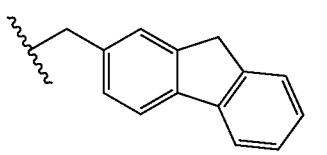 | 573 | +++ | A |
| 10 | 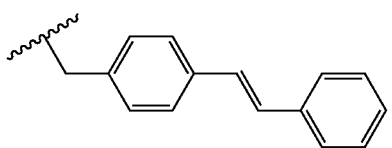 | 532 | +++ | B |
| 11 | 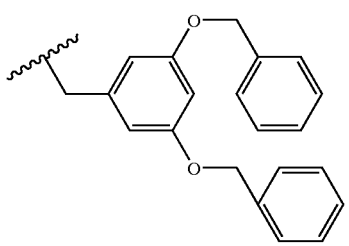 | 546 | +++ | A |
| 12 | | 656 | +++ | A |

TABLE 1-continued
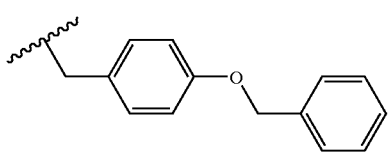
| Example No. | R³ | MS (M + H)⁺ | Displacement Rate (%) (at 10 μM) | MC4R IC$_{50}$ (μM) |
|---|---|---|---|---|
| 13 | 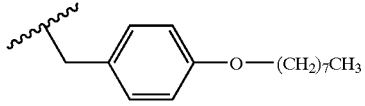 | 550 | +++ | B |
| 14 | 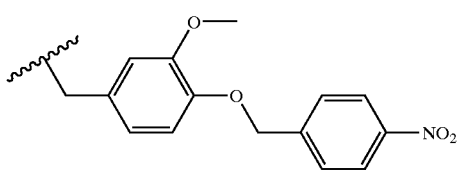 | 572 | +++ | A |
| 15 | 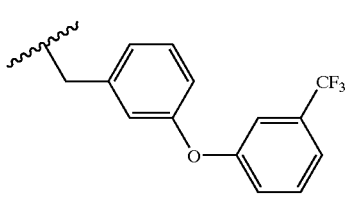 | 625 | +++ | B |
| 16 | 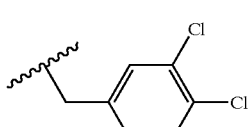 | 604 | +++ | A |
| 17 | 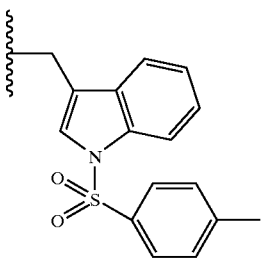 | 512 | +++ | B |
| 18 |  | 637 | +++ | A |

TABLE 1-continued
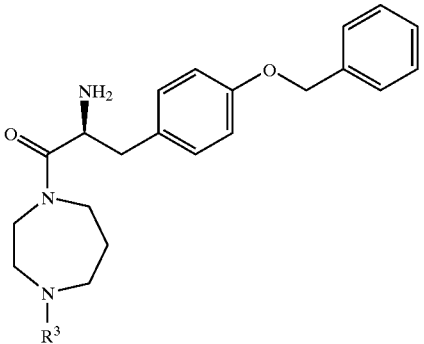
| Example No. | R³ | MS (M + H)⁺ | Displacement Rate (%) (at 10 μM) | MC4R IC$_{50}$ (μM) |
|---|---|---|---|---|
| 19 | 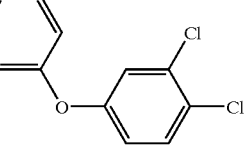 | 604 | +++ | A |
| 20 | 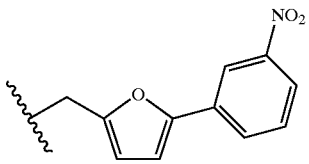 | 544 | +++ | C |
| 21 | 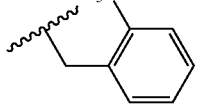 | 555 | +++ | B |
| 22 | 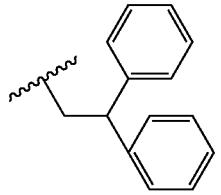 | 512 | +++ | C |
| 23 | 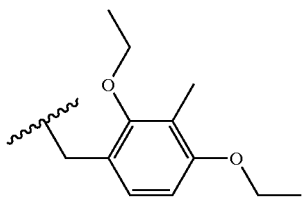 | 534 | +++ | C |
| 24 |  | 546 | +++ | A |

TABLE 1-continued

| Example No. | R³ | MS (M + H)⁺ | Displacement Rate (%) (at 10 μM) | MC4R IC$_{50}$ (μM) |
|---|---|---|---|---|
| 25 | 4-CF₃-benzyl | 512 | +++ | A |
| 26 | 3,5-di-tert-butyl-4-hydroxybenzyl | 572 | ++ | B |
| 27 | 4-(4-nitrobenzyloxy)benzyl | 595 | ++ | A |
| 28 | 2-fluoro-4-CF₃-benzyl | 530 | ++ | C |
| 29 | 3-methoxy-4-benzyloxybenzyl | 580 | ++ | B |
| 30 | 1,2,3,4-tetrahydronaphthalen-2-yl-methyl | 484 | ++ | C |

TABLE 1-continued
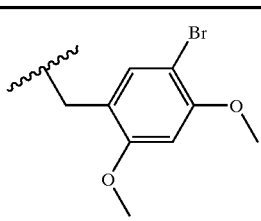
| Example No. | R³ | MS (M + H)⁺ | Displacement Rate (%) (at 10 μM) | MC4R IC$_{50}$ (μM) |
|---|---|---|---|---|
| 31 | 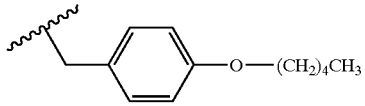 | 582 | ++ | B |
| 32 | 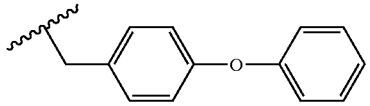 | 530 | ++ | A |
| 33 | 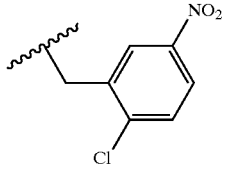 | 536 | ++ | B |
| 34 | 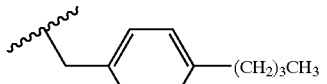 | 523 | ++ | C |
| 35 | 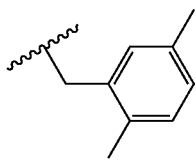 | 500 | ++ | B |
| 36 | | 472 | ++ | C |
| 37 | 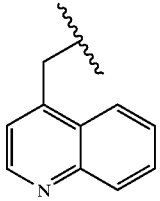 | 495 | ++ | C |

TABLE 1-continued

| Example No. | R³ | MS (M + H)⁺ | Displacement Rate (%) (at 10 μM) | MC4R IC$_{50}$ (μM) |
|---|---|---|---|---|
| 38 | 4-ethylbenzyl | 472 | ++ | C |
| 39 | 4-tert-butylbenzyl | 500 | ++ | B |
| 40 | 2-ethoxy-6-hydroxymethyl-phenyl (CH₂ linker, HO and OEt substituents) | 504 | ++ | C |
| 41 | 4-phenylcyclohexyl | 512 | ++ | C |
| 42 | 4-phenylbutyl | 472 | ++ | C |
| 43 | (2-methoxynaphthalen-1-yl)methyl | 524 | ++ | B |
| 44 | 2-methyl-3-(3-trifluoromethylphenyl)propyl | 540 | ++ | B |
| 45 | (5-ethylthiophen-2-yl)methyl | 478 | + | C |

TABLE 1-continued

| Example No. | R³ | MS (M + H)⁺ | Displacement Rate (%) (at 10 μM) | MC4R IC$_{50}$ (μM) |
|---|---|---|---|---|
| 46 | —(CH₂)₆CH₃ | 452 | + | C |
| 47 | naphthalen-1-ylmethyl | 494 | + | C |
| 48 | (3-methylthiophen-2-yl)methyl | 464 | + | C |
| 49 | 2-methyl-3-phenoxypropyl | 488 | + | C |
| 50 | 2-ethoxybenzyl | 488 | + | C |
| 51 | 1-(naphthalen-2-yl)ethyl | 494 | + | C |
| 52 | 2,4-dichlorobenzyl | 512 | + | C |
| 53 | cyclohexylmethyl | 450 | + | C |

TABLE 1-continued
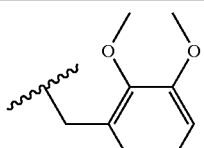
| Example No. | R³ | MS (M + H)⁺ | Displacement Rate (%) (at 10 μM) | MC4R IC$_{50}$ (μM) |
|---|---|---|---|---|
| 54 | 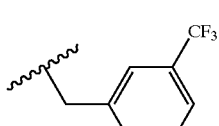 | 504 | + | C |
| 55 | 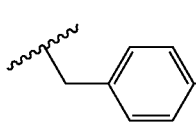 | 512 | + | C |
| 56 | 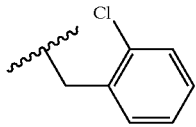 | 522 | + | C |
| 57 | 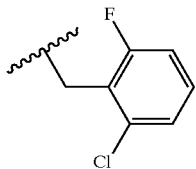 | 478 | + | C |
| 58 | 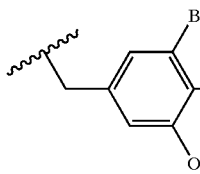 | 496 | + | C |
| 59 | 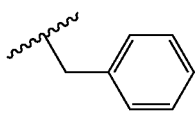 | 582 | + | C |
| 60 | 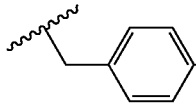 | 444 | + | C |
| 61 | | 489 | + | C |

TABLE 1-continued
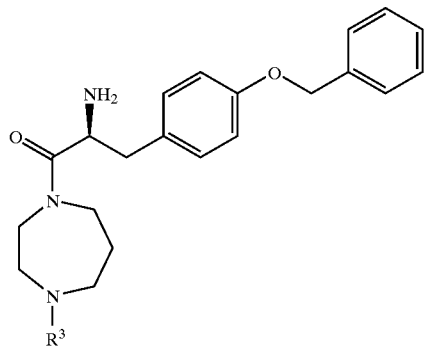
| Example No. | R³ | MS (M + H)⁺ | Displacement Rate (%) (at 10 μM) | MC4R IC₅₀ (μM) |
|---|---|---|---|---|
| 62 | 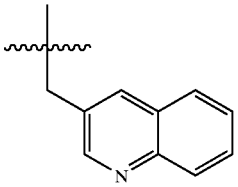 | 495 | + | C |
| 63 | 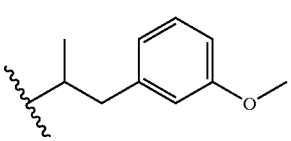 | 502 | + | C |
| 64 | 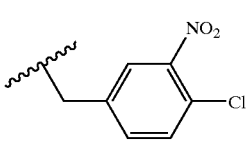 | 523 | + | C |
| 65 | 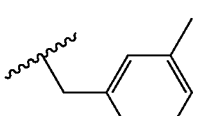 | 458 | + | C |
| 66 | 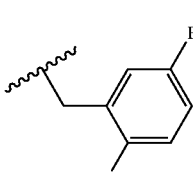 | 480 | + | C |
| 67 | 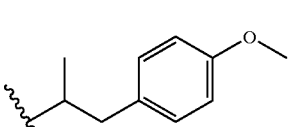 | 502 | + | C |
| 68 | 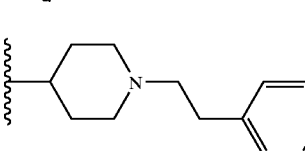 | 541 | + | C |

TABLE 1-continued
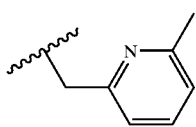
| Example No. | R³ | MS (M + H)⁺ | Displacement Rate (%) (at 10 μM) | MC4R IC$_{50}$ (μM) |
|---|---|---|---|---|
| 69 | 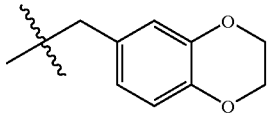 | 459 | + | C |
| 70 | 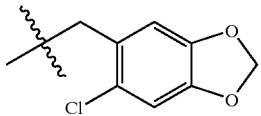 | 502 | + | C |
| 71 | 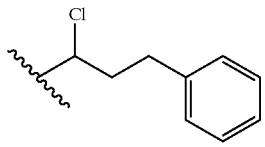 | 522 | + | C |
| 72 | 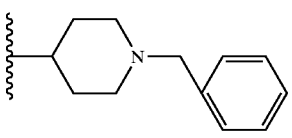 | 486 | + | C |
| 73 | 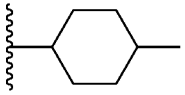 | 527 | + | C |
| 74 | 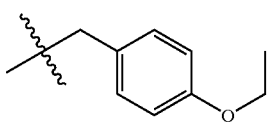 | 450 | + | C |
| 75 | 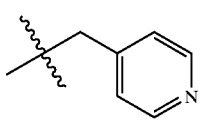 | 502 | + | C |
| 76 | | 445 | + | C |

TABLE 1-continued

| Example No. | R³ | MS (M + H)⁺ | Displacement Rate (%) (at 10 μM) | MC4R IC$_{50}$ (μM) |
|---|---|---|---|---|
| 77 | (6-nitro-1,3-benzodioxol-5-yl)methyl, branched at CH | 533 | + | C |
| 78 | (4-fluorophenyl)methyl, branched at CH | 462 | + | C |
| 79 | [4-(dimethylamino)phenyl]methyl, branched at CH | 487 | + | C |

TABLE 2

| Example No. | R³ | MS (M + H)⁺ | Displacement Rate (%) (at 10 μM) | MC4R IC$_{50}$ (μM) |
|---|---|---|---|---|
| 80 | {3-[4-(tert-butyl)phenoxy]phenyl}methyl | 578 | +++ | A |

TABLE 2-continued

| Example No. | R³ | MS (M + H)⁺ | Displacement Rate (%) (at 10 μM) | MC4R IC$_{50}$ (μM) |
|---|---|---|---|---|
| 81 | 4-chlorophenyl-furan-CH₂- | 530 | +++ | A |
| 82 | 2-(4-chlorophenylthio)benzyl- | 572 | +++ | A |
| 83 | fluoren-2-ylmethyl- | 518 | +++ | A |
| 84 | 4-phenoxybenzyl- | 522 | +++ | A |
| 85 | 3-(benzyloxy)benzyl- | 536 | +++ | A |
| 86 | 3-(3,5-dichlorophenoxy)benzyl- | 590 | +++ | A |

TABLE 2-continued
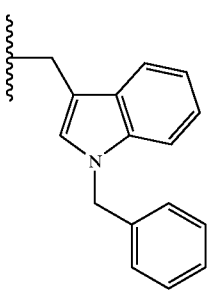
| Example No. | R³ | MS (M + H)⁺ | Displacement Rate (%) (at 10 μM) | MC4R IC$_{50}$ (μM) |
|---|---|---|---|---|
| 87 | 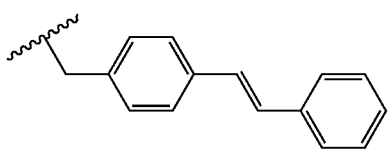 | 559 | +++ | A |
| 88 | 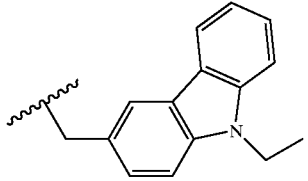 | 532 | +++ | A |
| 89 | 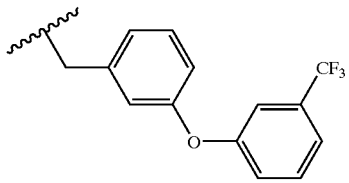 | 547 | +++ | A |
| 90 | 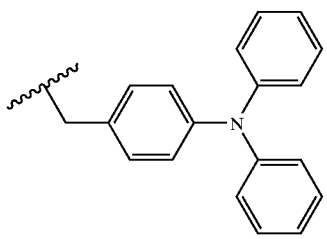 | 590 | +++ | A |
| 91 |  | 597 | +++ | A |

TABLE 2-continued

| Example No. | R³ | MS (M + H)⁺ | Displacement Rate (%) (at 10 μM) | MC4R IC$_{50}$ (μM) |
| --- | --- | --- | --- | --- |
| 92 | 3,5-di-tert-butyl-4-hydroxybenzyl | 558 | +++ | A |
| 93 | 2,3-dichlorobenzyl | 498 | +++ | A |
| 94 | 2-(trifluoromethyl)benzyl | 498 | +++ | B |
| 95 | 4-phenylbenzyl (biphenyl) | 506 | +++ | A |
| 96 | 4-butylbenzyl | 486 | +++ | A |
| 97 | 1-tosyl-1H-indol-3-ylmethyl | 623 | +++ | A |
| 98 | 2,4-bis(trifluoromethyl)benzyl | 566 | +++ | B |

TABLE 2-continued

| Example No. | R³ | MS (M + H)⁺ | Displacement Rate (%) (at 10 μM) | MC4R IC$_{50}$ (μM) |
|---|---|---|---|---|
| 99 | 4-pentyloxybenzyl | 516 | +++ | A |
| 100 | 9-anthracenylmethyl | 530 | +++ | B |
| 101 | 3,5-bis(trifluoromethyl)benzyl | 566 | +++ | A |
| 102 | 2,2-diphenylethyl | 520 | +++ | B |
| 103 | 3-phenoxybenzyl | 522 | +++ | A |
| 104 | 2,5-diethoxy-3-methylbenzyl | 532 | +++ | B |

TABLE 2-continued

| Example No. | R³ | MS (M + H)⁺ | Displacement Rate (%) (at 10 μM) | MC4R IC$_{50}$ (μM) |
|---|---|---|---|---|
| 105 | 2-naphthylmethyl (with methyl) | 480 | ++ | A |
| 106 | (2-methoxynaphthalen-1-yl)methyl | 510 | ++ | B |
| 107 | (2,5-dimethylphenyl)methyl | 458 | ++ | B |
| 108 | (2,4-bis(trifluoromethyl)phenyl)methyl | 516 | ++ | C |
| 109 | (biphenyl-2-yl)methyl | 506 | ++ | C |
| 110 | (4-((4-nitrobenzyl)oxy)phenyl)methyl | 581 | ++ | A |
| 111 | (2-nitrophenyl)methyl | 475 | ++ | C |

TABLE 2-continued

| Example No. | R³ | MS (M + H)⁺ | Displacement Rate (%) (at 10 μM) | MC4R IC$_{50}$ (μM) |
|---|---|---|---|---|
| 112 | 4-tert-butylbenzyl | 486 | ++ | B |
| 113 | cyclohexylmethyl | 436 | ++ | A |
| 114 | 4-chloro-3-nitrobenzyl | 509 | ++ | C |
| 115 | 4-benzyloxy-3-methoxybenzyl | 566 | ++ | C |
| 116 | 2-ethoxybenzyl | 474 | ++ | B |
| 117 | 3-(2-ethoxy)-2-hydroxybenzyl | 490 | ++ | C |
| 118 | 4-phenylcyclohexyl | 498 | ++ | C |

TABLE 2-continued

[Structure: central scaffold with NH₂, carbonyl, benzyl ether on para-phenyl, linked to piperazine N-R³]

| Example No. | R³ | MS (M + H)⁺ | Displacement Rate (%) (at 10 μM) | MC4R IC$_{50}$ (μM) |
|---|---|---|---|---|
| 119 | 2,4-dichlorobenzyl | 498 | ++ | C |
| 120 | 2,3-difluorobenzyl | 466 | ++ | C |
| 121 | 3-bromo-4,5-dimethoxybenzyl | 568 | ++ | B |
| 122 | –(CH₂)₆CH₃ | 438 | ++ | B |
| 123 | 3-(trifluoromethyl)benzyl | 498 | ++ | C |
| 124 | (6-chloro-1,3-benzodioxol-5-yl)methyl | 508 | ++ | C |
| 125 | 4-(methylthio)benzyl | 476 | ++ | B |
| 126 | 4-propoxybenzyl | 488 | ++ | B |

TABLE 2-continued

| Example No. | R³ | MS (M + H)⁺ | Displacement Rate (%) (at 10 μM) | MC4R IC$_{50}$ (μM) |
|---|---|---|---|---|
| 127 | (1-naphthylmethyl-CH₂-) | 480 | ++ | n.t. |
| 128 | (3-methylthiophen-2-yl)ethyl | 450 | + | C |
| 129 | (4-bromobenzyl), gem-dimethyl | 508 | + | C |
| 130 | (2-bromo-4,5-dimethoxybenzyl) | 568 | + | C |
| 131 | (5-ethylthiophen-2-yl)methyl | 464 | + | C |
| 132 | 3-(4-methoxyphenyl)-1,1-dimethylpropyl | 502 | + | C |
| 133 | 4-(octyloxy)benzyl | 558 | + | A |

TABLE 2-continued
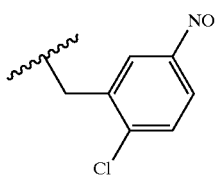
| Example No. | R³ | MS (M + H)⁺ | Displacement Rate (%) (at 10 μM) | MC4R IC₅₀ (μM) |
| --- | --- | --- | --- | --- |
| 134 | 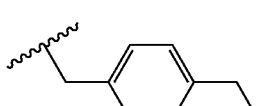 | 509 | + | B |
| 135 | 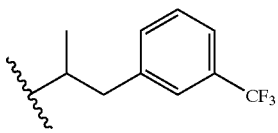 | 458 | + | C |
| 136 | 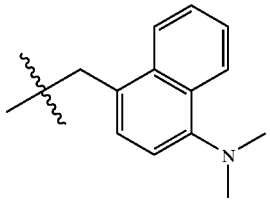 | 526 | + | C |
| 137 | 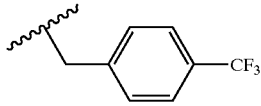 | 523 | + | C |
| 138 | 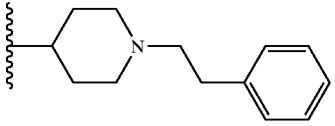 | 498 | + | C |
| 139 | 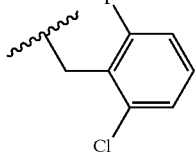 | 527 | + | B |
| 140 |  | 482 | + | C |

TABLE 2-continued

| Example No. | R³ | MS (M + H)⁺ | Displacement Rate (%) (at 10 μM) | MC4R IC$_{50}$ (μM) |
|---|---|---|---|---|
| 141 | benzyl | 430 | + | C |
| 142 | 2,6-difluorobenzyl (gem-dimethyl) | 466 | + | C |
| 143 | CH(CH₃)₂ | 382 | + | C |
| 144 | 3-methylbenzyl | 444 | + | C |
| 145 | 2,5-difluorobenzyl | 466 | + | C |
| 146 | CH₂CH(CH₃)₂ | 396 | + | C |
| 147 | 3-phenylpropyl | 458 | + | C |
| 148 | 3-hydroxy-4-nitrobenzyl | 491 | + | C |
| 149 | 4-nitrobenzyl | 475 | + | C |

TABLE 2-continued

| Example No. | R³ | MS (M + H)⁺ | Displacement Rate (%) (at 10 μM) | MC4R IC$_{50}$ (μM) |
|---|---|---|---|---|
| 150 | (3-methoxy-4-(4-nitrobenzyloxy)benzyl) | 611 | + | B |
| 151 | (furan-2-ylmethyl) | 420 | + | C |
| 152 | (3-nitrobenzyl) | 475 | + | C |
| 153 | (2,4-difluorobenzyl) | 466 | + | C |
| 154 | (6-nitrobenzo[d][1,3]dioxol-5-ylmethyl) | 519 | + | C |
| 155 | (1-benzylpiperidin-4-yl) | 513 | + | C |
| 156 | (2,3-dihydrobenzo[b][1,4]dioxin-6-ylmethyl) | 488 | + | C |
| 157 | (1-phenylethyl) | 444 | + | C |

TABLE 2-continued

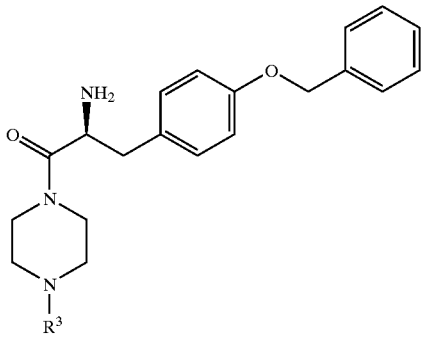

| Example No. | R³ | MS (M + H)⁺ | Displacement Rate (%) (at 10 μM) | MC4R IC$_{50}$ (μM) |
|---|---|---|---|---|
| 158 | ⟨cyclopentylmethyl⟩ | 408 | + | C | n.t. = not tested

EXAMPLE 159

N-(2,3-Dichlorophenylmethyl)-N'-[O-(phenylmethyl)-L-tyrosine]-piperazine amide

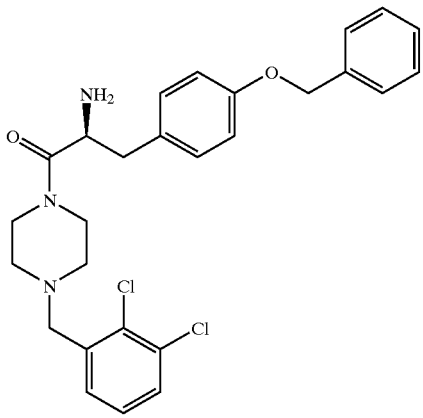

To a suspension of N-(2,3-dichlorophenylmethyl) piperazine, dihydrochloride salt [Intermediate (4), (519.1 mg, 1.64 mmol, 1.0 equiv.)] and the 4-nitrophenol ester of N-(tert-butyloxycarbonyl)-O-(phenylmethyl)-L-tyrosine (806 mg, 1.64 mmol, 1.0 equiv.) was added dropwise diisopropyl ethylamine (Hunig's base, 1 mL, excess). The reaction mixture became a clear, yellow solution which was stirred overnight. The reaction mixture was then washed with 1 N aqueous NaOH, until colorless. The organic layer was dried over $Na_2SO_4$, filtered and the filtrate was concentrated in vacuo to afford a colorless foam. The colorless foam was then dissolved in MeOH and treated with 1 M HCl/Et$_2$O overnight. Concentration in vacuo to dryness afforded essentially pure product. The product was taken up in $CH_2Cl_2$ and washed with 1 N NaOH and water, dried over $Na_2SO_4$ and concentrated in vacuo. Purification by flash column chromatography on silica afforded the free base of the titled compound as a colorless oil: ¹H NMR (CDCl₃) δ 7.46–7.34 (m, 7H), 7.17 (t, J=7.8 Hz, 1H), 7.11 (d, J=8.2 Hz, 2H), 6.92 (d, J=8.2 Hz, 1H), 5.06 (s, 2H), 3.92 (t, J=6.6 Hz, 1H), 3.64–3.56 (m, 4H), 3.34 (m, 1H), 3.12 (m, 1H), 2.88 (q, J=6.7 Hz, 1H), 2.75 (q, J=6.7 Hz, 1H), 2.46 (m, 1H), 2.37 (m, 2H), 2.00 (m, 1H), 1.90 (s, 2H); ¹³C NMR (CDCl₃) δ 173.3, 158.0, 138.1, 137.2, 133.5, 132.7, 130.9, 130.6, 130.1, 129.4, 128.8, 128.2, 127.7, 127.2, 115.3, 70.4, 60.0, 53.0, 52.7, 45.5, 42.3; MS Calcd for $[C_{27}H_{29}Cl_2N_3O_2+H]^+$: 498. found: 498.

The dihydrochloride salt of the titled compound was prepared as follows: The free base of the titled compound (obtained as described above) was dissolved in MeOH and made acidic with HCl/Et$_2$O (1M). Concentration in vacuo afforded the dihydrochloride salt of the titled compound as a white solid: $[\alpha]_D^{23}$=+24.70 (c 0.429, MeOH); ¹³C NMR (CD₃OD) δ 168.9, 160.3, 138.6, 135.3, 134.1, 133.6, 132.3, 130.5, 129.9, 129.7, 129.2, 128.8, 127.5, 116.9, 71.3, 59.1, 52.9, 52.6, 52.2, 43.6, 40.2, 38.1, 30.9;

Anal Calcd for $C_{27}H_{29}Cl_2N_3O_2$ · C, 55.31; H, 5.61; N, 7.17. 2HCl · (0.81)H$_2$O:
Found: C, 55.31; H, 5.61; N, 6.98.

EXAMPLE 160

(N,N-Dimethyl)-O-(phenylmethyl)-L-tyrosine, 1-[4-(2,3-dichlorophenyl)methyl]piperazine amide

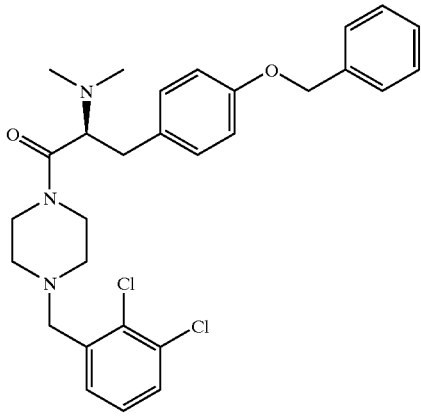

To a solution of N-(2,3-dichlorophenylmethyl)-N'-[O-(phenylmethyl)-L-tyrosine]piperazine amide, dihydrochloride salt [Compound of Example 159, (400 mg, 0.70 mmol)] in MeOH (10 mL) was added consecutively paraformaldehyde (excess), ZnCl$_2$ (1.0 equiv) and NaBH$_3$CN (1.0 equiv) at room temperature. The reaction mixture was then stirred at room temperature overnight and was diluted with EtOAc. The organic solution was washed with water and brine, dried over Na$_2$SO$_4$, filtered and the filtrate concentrated in vacuo to give the titled compound (313 mg, 85%) as a colorless oil: $^1$H NMR (CDCl$_3$) δ 7.47–7.30 (m, 7H), 7.21–7.11 (m, 3H), 6.90 (d, J=8.6 Hz, 2H), 5.06 (s, 2H), 3.66–3.55 (m, 3H), 3.52 (s, 2H), 3.50–3.34 (m, 1H), 3.23–3.10 (m, 2H), 2.86 (dd, J=12.7 and 3.4 Hz, 1H), 2.41 (s, 6H), 2.41–2.26 (m, 3H), 2.01–1.88 (m, 1H); $^{13}$C NMR (CDCl$_3$) δ 169.73, 157.58, 138.20, 137.27, 133.35, 132.60, 131.36, 130.68, 129.36, 128.77, 128.69, 128.13, 127.66, 127.18, 115.04, 70.25, 65.93, 59.99, 53.32, 53.21, 45.91, 42.02, 41.81, 32.66; MS Calcd for $[C_{29}H_{33}Cl_2N_3O_2+H]^+$: 526. found: 526.

EXAMPLE 161

(±)-N-Methyl-O-(phenylmethyl)tyrosine,1-[4-(2,3-dichlorophenyl)methyl]piperazine amide

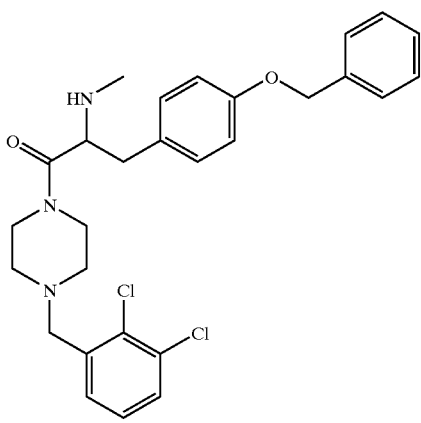

To a suspension of NaH in THF (5 mL) cooled to 0° C. was added dropwise a solution of N-(tert-butyloxycarbonyl)-O-(phenylmethyl)-L-tyrosine, 1-[4-(2,3-dichlorophenyl)methyl]piperazine amide (N-Boc derivative of Example 159) (339 mg, 1.0 equiv). Methyl iodide (402 mg, 5 equiv) was then added to the reaction mixture via syringe. After the reaction was stirred at 0° C. for 30 minutes, it was warmed up to room temperature and stirred for 3 hours. An excess of methyl iodide and NaH was added to the reaction mixture (to achieve approximately 70% conversion) over 48 hours. After aqueous work up, the mixture was directly treated with HCl/Et$_2$O in MeOH to afford the racemized titled product along with racemized O-(phenylmethyl)-L-tyrosine, 1-[4-(2,3-dichlorophenyl)methyl]piperazine amide (wherein the amine was not methylated). The mixture was then stirred with polymer bound benzaldehyde resin and filtered, thereby removing the racemized O-(phenylmethyl)-L-tyrosine, 1-[4-(2,3-dichlorophenyl)methyl]piperazine amide. The filtrate was concentrated in vacuo and the residue was further purified by preparative HPLC to afford the racemic titled compound, bis trifluoroacetic acid salt (100 mg) as a colorless oil (HPLC purity:100%): MS Calcd for $[C_{28}H_{31}Cl_2N_3O_2+H]^+$: 512. found: 512.

EXAMPLE 162

N-Methyl-O-(phenylmethyl)-L-tyrosine, 1-[4-[(2,3-dichlorophenyl)methyl]piperazine]amide

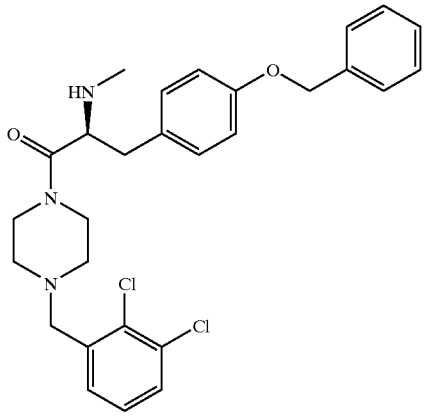

To a suspension of 1-(2,3-dichlorophenylmethyl)piperazine, dihydrochloride salt [Intermediate (4), (427 mg, 1.0 equiv)] and N-(tert-butyloxycarbonyl)-N-methyl-O-(phenylmethyl)-L-tyrosine (519 mg, 1.35 mmol, 1.0 equiv) in CH$_2$Cl$_2$ was added Et$_3$N (4 equiv), DCC (278 mg, 1.0 equiv) and DMAP (16 mg, 0.10 equiv) at room temperature. The reaction mixture was then stirred overnight and washed with water and brine. The organic solution was dried with Na$_2$SO$_4$, filtered and the filtrate was concentrated in vacuo. The residue was purified by flash column chromatography on silica (55% yield). The tert-butyloxycarbonyl protected intermediate was then treated with HCl/Et$_2$O in MeOH to effect the deprotection of the tert-butyloxycarbonyl group to afford the crude titled product as a hydrochloride salt. A suspension of the crude titled product, hydrochloride salt in CH$_2$Cl$_2$ was then made basic with aqueous NaOH (10 N). The organic layer was separated, dried over Na$_2$SO$_4$, filtered and the filtrate concentrated in vacuo. After purification of the residue by flash column chromatography on silica [10:1:0.1 CH$_2$Cl$_2$/MeOH/NH$_3$ ((2 M) in MeOH)], the free base of the titled compound was obtained as a colorless oil: $^1$H NMR (CDCl$_3$) δ 7.44–7.28 (m, 7H), 7.20–7.08 (m, 3H), 6.90 (d, J=8.6 Hz, 2H), 5.06 (s, 2H), 3.69–3.56 (m, 3H), 3.51 (s, 2H), 3.40–3.20 (m, 1H), 3.04–2.96 (m, 1H), 2.93 (dd, J=13.2 and 5.4 Hz, 1H), 2.76 (dd, J=13.2 and 9.2 Hz, 1H), 2.46–2.32 (m, 2H), 2.32 (s, 3H), 2.32–2.20 (m, 1H), 2.06 (br, 1H), 1.90–1.74 (m, 1H); $^{13}C$ NMR (CDCl$_3$) δ 172.84, 157.92, 138.14, 137.26, 133.46, 132.70, 130.61, 130.28, 129.36, 128.80, 128.74, 128.17, 127.64, 127.21, 115.23, 70.35, 61.18, 60.02, 53.14, 53.09, 45.32, 42.16, 39.85, 34.77; MS Calcd for $[C_{28}H_{31}Cl_2N_3O_2+H]^+$: 512. found: 512.

The dihydrochloride salt of the titled compound was prepared as follows. The purified free base of the titled compound in CH$_2$Cl$_2$ was made acidic with HCl/Et$_2$O (1 M). After concentration under high vacuum, the dihydrochloride salt of the titled compound was obtained as a white solid: $^{13}C$ NMR (CDCl$_3$) δ 167.94, 160.34, 138.55, 135.37, 135.33, 134.13, 133.63, 132.42, 130.39, 129.88, 129.71, 129.18, 128.85, 126.96, 116.89, 71.32, 60.00, 59.08, 52.75, 52.54, 43.47, 40.10, 37.07, 32.47; HPLC purity: 100%; MS Calcd for $[C_{28}H_{31}Cl_2N_3O_2+H]^{+\cdot}$ 512. found: 512; $[\alpha]_D^{23}$=+40.81 (c 0.328, CHCl$_3$).

EXAMPLE 163

N-Ethyl-O-(phenylmethyl)-L-tyrosine, 1-[4-[(2,3-dichlorophenyl)-methyl]piperazine]amide Step A: N-[(2,4-Dinitrophenyl)sulfonyl]-O-(phenylmethyl)-L-tyrosine, 1-[4-[(2,3-dichlorophenyl)methyl]piperazine]amide

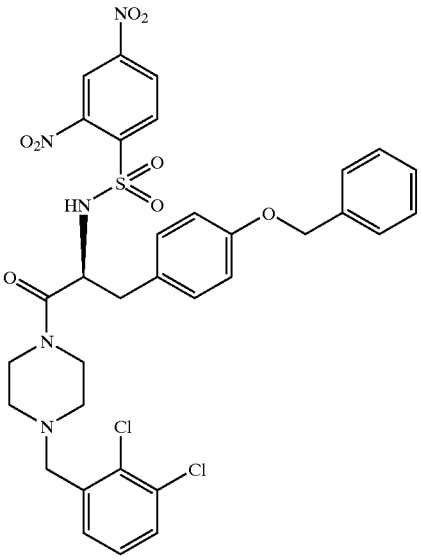

To a suspension of crude N-(2,3-dichlorophenylmethyl)-N'-[O-(phenylmethyl)-L-tyrosine]-piperazine amide [compound of Example 159, (1.54 g, 2.69 mmol, 1.0 equiv)], in anhydrous CH$_2$Cl$_2$ (130 mL) at room temperature was added Et$_3$N (1.16 mL, 8.34 mmol, 3.1 equiv) followed by 2,4-dinitrophenylsulfonyl chloride (725 mg, 2.72 mmol, 1.01 equiv). The resulting yellow mixture was stirred at room temperature for 1 hour and was then diluted with EtOAc. The organic solution was washed with aqueous NaOH (0.5 N), water and brine, dried over Na$_2$SO$_4$, filtered, and the filtrate concentrated in vacuo. Purification of the residue by flash column chromatography on silica (10:1 CH$_2$Cl$_2$/EtOAc) afforded the titled sulfonamide intermediate (1.06 g, 54%) as a dense yellow oil: HPLC purity: 100%; MS Calcd for $[C_{33}H_{31}Cl_2N_5O_8S +H]^+$: 728. found: 728.

Step B: N-Ethyl-N-[(2,4-dinitrophenyl)sulfonyl]-O-(phenylmethyl)-L-tyrosine, 1-[4-[(2,3-dichlorophenyl)methyl]piperazine]amide

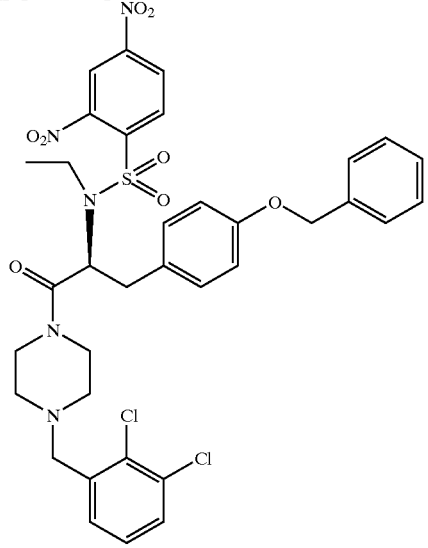

To an oven-dried test tube with a stir bar under nitrogen charged with excess ethanol (2–3 equiv) and triphenylphosphine (24.5 mg, 2.0 equiv) in CH$_2$Cl$_2$ (1 mL) was added a solution of the sulfonamide intermediate (from Step A, 34.0 mg, 1.0 equiv) in CH$_2$Cl$_2$ (1 mL). The reaction mixture was stirred at room temperature, and to it was added dropwise DIAD (18.5 μL, 2.0 equiv). The reaction was allowed to stir at room temperature overnight. Examination of the mixture by HPLC showed greater than 95% conversion to the desired titled intermediate shown above. MS Calcd for $[C_{35}H_{35}Cl_2N_5O_8S+H]^+$: 756. found: 756. The crude reaction mixture was used in the next reaction without any further purification.

Step C: N-Ethyl-O-(phenylmethyl)-L-tyrosine, 1-[4-[(2,3-dichlorophenyl)methyl]piperazine]amide

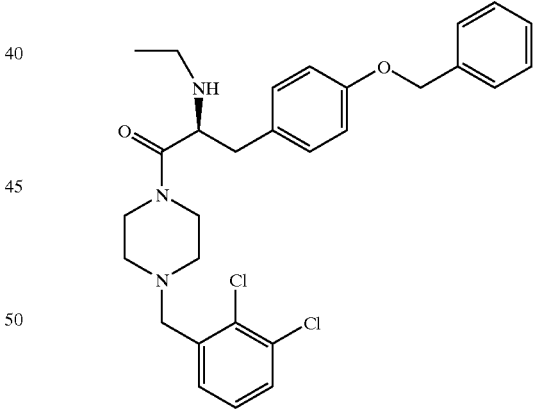

Excess Et$_3$N (3–5 equiv) and mercaptoacetic acid (3–5 equiv) were directly added dropwise to the reaction mixture containing the intermediate N-ethyl-N-[(2,4-dinitrophenyl)sulfonyl]-O-(phenylmethyl)-L-tyrosine, 1-[4-[(2,3-dichlorophenyl)methyl]piperazine]amide (from Step B, above). The reaction mixture was stirred at room temperature for 1 hour and was then diluted with more CH$_2$Cl$_2$. The organic solution was washed with aqueous NaOH (1 N), brine, dried over Na$_2$SO$_4$, filtered, and the filtrate concentrated in vacuo. Purification of the residue by flash column chromatography on silica afforded the free base of the titled compound (19.7 mg, 80% for two steps) as a colorless oil: HPLC purity: 100%; $^1H$ NMR (CDCl$_3$) δ 7.45–7.24 (m, 7H), 7.18–7.08 (m, 3H), 6.89 (d, J=8.6 Hz, 2H), 5.05 (s, 2H), 3.79 (dd, J=9.8, 5.0 Hz, 1H), 3.60–3.54 (m, 2H), 3.49 (s, 2H), 3.25–3.16 (m, 1H), 3.09 (dd, J=13.0 and 5.0 Hz, 1H), 2.93–2.85 (m, 1H), 2.78 (dd, J=13.0 and 9.8 Hz, 1H), 2.63–2.46 (m, 3H), 2.42–2.17 (m, 3H), 1.79–1.68 (m, 1H), 1.12 (t, J=7.1 Hz, 3H); $^{13}$C NMR (CDCl$_3$) δ 172.71, 157.97, 138.11, 137.24, 133.47, 132.71, 130.69, 130.08, 129.36, 128.80, 128.72, 128.17, 127.64, 127.19, 115.24, 70.37, 60.00, 59.21, 53.06, 53.00, 45.33, 42.40, 42.15, 39.87, 15.37; MS Calcd for $[C_{29}H_{33}Cl_2N_3O_2+H]^+$: 526. found: 526.

The free base of the titled compound was dissolved in CH$_2$Cl$_2$ and the solution was made acidic with HCl/Et$_2$O (1 M). After concentration in vacuo, the dihydrochloride salt of the titled compound was obtained as an off-white solid: HPLC purity: 100%; MS Calcd for $[C_{29}H_{33}Cl_2N_3O_2+H]^+$: 526. found: 526.

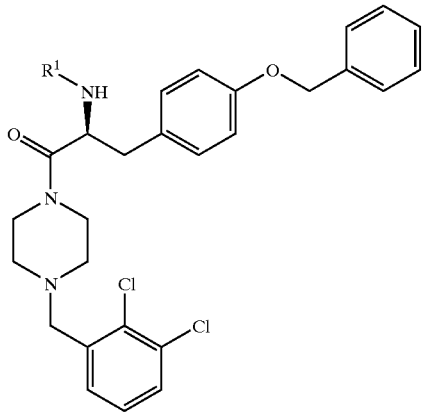

General Procedure. The synthesis of Examples 164–176 was accomplished starting from the common sulfonamide intermediate, N-ethyl-N-[(2,4-dinitrophenyl)sulfonyl]-O-(phenylmethyl)-L-tyrosine, 1-[4-(2,3-dichlorophenyl)methyl]piperazine amide (compound of Example 163, Step B), and the corresponding alcohols, R$^1$OH. The synthesis followed the same procedures as described for the synthesis of the compound of Example 163, Step C, however a modified work up procedure was adopted. Thus after carrying out the desulfonylation reaction as described in Step C of Example 163, aqueous NaOH (1 N, 2 mL) was added to the reaction mixture and the mixture was stirred for a few minutes. The organic solution was then pipetted out and passed through a celite cartridge. The aqueous solution was extracted twice with CH$_2$Cl$_2$ (2×2 mL) and the extracts were used to rinse the celite cartridge twice. The ed CH$_2$Cl$_2$ solutions were concentrated in vacuo. The crude product was then dissolved in CH$_2$Cl$_2$ and was loaded onto an SCX cartridge. The cartridge was washed with CH$_2$Cl$_2$ and MeOH (3 times each). The product was eluted from the SCX cartridge with NH$_3$/MeOH (2.0 M). After the eluent was concentrated in vacuo, the resulting product was analyzed by HPLC and further purified by preparative HPLC if the purity was less than 95%.

TABLE 3

| Example No. | R$^1$ | M.S. (M + H)$^+$ | Displacement Rate (%) (at 10 μM) | MC4R IC$_{50}$ (μM) |
|---|---|---|---|---|
| 164 | H | 498 | +++ | A |
| 165 | CH$_3$ | 512 | n.t. | A |
| 166 | CH$_3$CH$_2$ | 526 | +++ | A |
| 167 | CH$_3$(CH$_2$)$_2$ | 540 | +++ | A |
| 168 | (CH$_3$)$_2$CH | 540 | ++ | A |
| 169 | CH$_3$(CH$_2$)$_3$ | 554 | +++ | A |
| 170 | (C$_6$H$_5$)CH$_2$— | 588 | ++ | C |
| 171 | (C$_6$H$_5$)(CH$_2$)$_2$— | 602 | ++ | C |

TABLE 3-continued

| Example No. | R¹ | M.S. (M + H)⁺ | Displacement Rate (%) (at 10 μM) | MC4R IC$_{50}$ (μM) |
|---|---|---|---|---|
| 172 | morpholine-N-CH₂CH₂CH₂- | 611 | ++ | B |
| 173 | morpholine-N-CH₂CH₂CH₂CH₂- | 625 | +++ | A |
| 174 | (CH₃)₂N-CH₂CH₂CH₂- | 583 | +++ | A |
| 175 | (CH₃)₂N-CH₂CH₂- | 569 | +++ | A |
| 176 | piperidine-N-CH₂CH₂- | 609 | +++ | A | n.t. = not tested

EXAMPLE 177

O-[2-(3-Methoxyphenyl)ethyl]-L-tyrosine, 1-[4-(2,3-dichlorophenyl)methyl)]piperazine amide

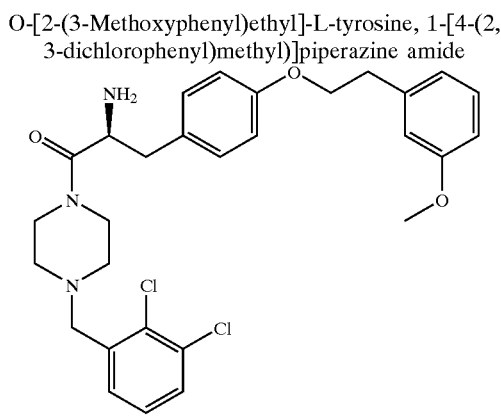

To a solution of N-(tert-butyloxycarbonyl)-L-tyrosine, 1-[4-[(2,3-dichlorophenyl)methyl)]piperazine]amide [Intermediate (5), (20 mg, 0.039 mmol, 1.0 equiv.)], PPh$_3$ (20.6 mg, 0.078 mmol, 2.0 equiv.), and (3-methoxyphenyl)ethanol (0.078 mmol, 2.0 equiv.) in CH$_2$Cl$_2$ (1 mL) was added DIAD (15.5 µL, 0.078 mmol) dropwise at room temperature. After stirring overnight, the reaction mixture was passed through an SCX cartridge, which was then washed with CH$_2$Cl$_2$ (6 mL), MeOH (6 mL) and CH$_2$Cl$_2$ (6 mL). The SCX cartridge was then eluted with 2M NH$_3$ in MeOH (6 mL) and the eluent was concentrated in vacuo. The residue was diluted with MeOH (1 mL) and treated with 1 M HCl/ether overnight. The reaction mixture was concentrated in vacuo and the residue was then redissolved in MeOH and purified by preparative HPLC to afford the titled product as a bis-trifluoroacetic acid salt: $^1$H NMR (CD$_3$OD) δ 7.51 (d, J=8.0 Hz, 1H), 7.42 (d, J=7.4 Hz, 1H), 7.24 (t, J=7.2 Hz, 1H), 7.14 (t, J=7.9 Hz, 1H), 7.07 (d, J=8.0 Hz, 2H), 6.86–6.78 (m, 4H), 6.63 (d, J=7.2 Hz, 1H), 4.54 (br, 1H), 4.13 (t, J=6.7 Hz, 2H), 4.12–4.02 (br, 2H), 3.71 (s, 3H), 3.44–3.32 (br, 2H), 3.26–3.04 (m, 6H), 3.04 (t, J=6.8 Hz, 2H), 2.96–2.84 (m, 2H); $^{13}$C NMR (CD$_3$OD) δ 167.85, 159.90, 159.08, 139.93, 134.44, 134.14, 132.81, 131.66, 131.08, 129.63, 128.73, 128.51, 125.77, 121.50, 115.37, 115.09, 111.97, 77.42, 68.98, 57.56, 55.30, 51.08, 50.77, 42.70, 39.23, 37.35, 35.93; MS Calcd for [C$_{29}$H$_{33}$Cl$_2$N$_3$O$_3$+H]$^+$: 544. found: 544.

EXAMPLES 178–287

The general procedure for the synthesis of Examples 178–287 is the same procedure as described for the synthesis of Example 177 starting from N-(tert-butyloxycarbonyl)-L-tyrosine, 1-[4-[(2,3-dichlorophenyl)methyl)]piperazine] amide (Intermediate 5) and an appropriate alcohol. All the final products were purified by preparative HPLC and characterized by LCMS, HPLC and LRMS. The individual mass observed (M+H)$^+$ and biological activity for Examples 178–287 are provided in Tables 4–8.

TABLE 4

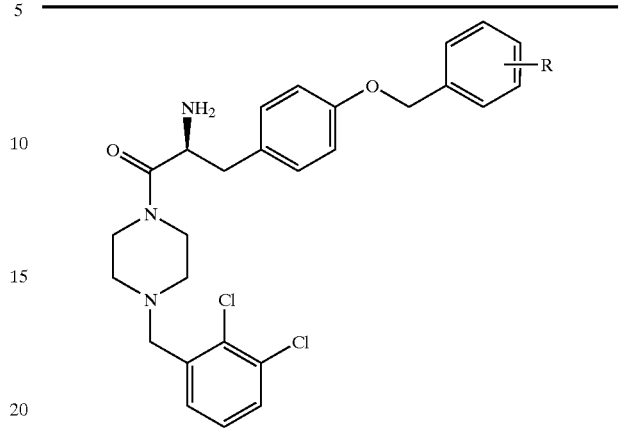

| Example No. | R | M.S. (M + H)$^+$ | Displacement Rate (%) (at 10 µM) | MC4R IC$_{50}$(µM) |
|---|---|---|---|---|
| 178 | H | 498 | +++ | A |
| 179 | 2-Br | 577 | +++ | A |
| 180 | 3-F | 517 | +++ | A |
| 181 | 4-CF$_3$ | 567 | +++ | A |
| 182 | 2-CF$_3$ | 567 | +++ | A |
| 183 | 4-Cl | 533 | +++ | A |
| 184 | 4-CH$_3$(CH$_2$)$_3$ | 555 | +++ | A |
| 185 | 2,3,4,5,6-F$_5$ | 589 | +++ | A |
| 186 | 4-Br | 577 | +++ | A |
| 187 | 3-CF$_3$ | 567 | +++ | B |
| 188 | 4-F | 517 | +++ | A |
| 189 | 3-Cl, 5-Cl | 567 | +++ | A |
| 190 | 3-CH$_3$, 5-CH$_3$ | 527 | +++ | B |
| 191 | 3-CH$_3$, 4-CH$_3$ | 527 | +++ | A |
| 192 | 4-CH$_3$ | 513 | +++ | A |
| 193 | 3-(C$_6$H$_5$O) | 591 | +++ | A |
| 194 | 3-CH$_3$O, 5-CH$_3$O | 559 | +++ | B |
| 195 | 4-(CH$_3$)$_2$CH | 541 | +++ | A |
| 196 | 2-F, 4-F | 535 | +++ | A |
| 197 | 3-Br | 577 | +++ | A |
| 198 | 4-C$_6$H$_5$ | 575 | +++ | A |
| 199 | 3-CF$_3$, 5-CF$_3$ | 635 | +++ | B |
| 200 | 2-Cl, 4-Cl | 567 | +++ | A |
| 201 | 4-(CH$_3$)$_3$C | 555 | +++ | A |
| 202 | 2-CH$_3$, 5-CH$_3$ | 527 | +++ | B |
| 203 | 3-CH$_3$O | 529 | +++ | B |
| 204 | 3-Cl, 4-Cl | 567 | +++ | A |
| 205 | 2-F, 6-F | 535 | +++ | B |
| 206 | 3-(C$_6$H$_5$CH$_2$O) | 605 | +++ | A |
| 207 | 3-CH$_3$O 3-(C$_6$H$_5$CH$_2$O) | 635 | +++ | B |
| 208 | 4-(C$_6$H$_5$CH$_2$O) | 605 | +++ | B |
| 209 | 4-CH$_3$CH$_2$O | 544 | +++ | B |
| 210 | 2-Cl | 533 | +++ | B |
| 211 | 2-[C$_6$H$_5$)CH$_2$)$_2$] | 603 | +++ | A |
| 212 | 2-Cl, 5-Cl | 567 | +++ | A |
| 213 | 3-CH$_3$ | 513 | +++ | A |
| 214 | 2-C$_6$H$_5$ | 575 | +++ | A |
| 215 | 2-(C$_6$H$_5$CH$_2$) | 589 | +++ | A |
| 216 | 2-CH$_3$ | 513 | +++ | B |
| 217 | 3,4-(Benzo) | 549 | +++ | A |
| 218 | 2,3-(Benzo) | 549 | +++ | B |
| 219 | 4-Cl, 5-NO$_2$ | 578 | +++ | A |
| 220 | 4-CH$_3$CH$_2$ | 527 | +++ | A |
| 221 | 2-(CH$_3$CH$_2$O) | 543 | +++ | B |
| 222 | 2-Cl, 6-F | 551 | +++ | B |
| 223 | 4-NO$_2$ | 544 | +++ | B |
| 224 | 4-CH$_3$S | 545 | ++ | B |
| 225 | 4-CH$_3$O | 529 | ++ | C |
| 226 | 2-Cl, 6-Cl | 567 | ++ | B |

TABLE 4-continued

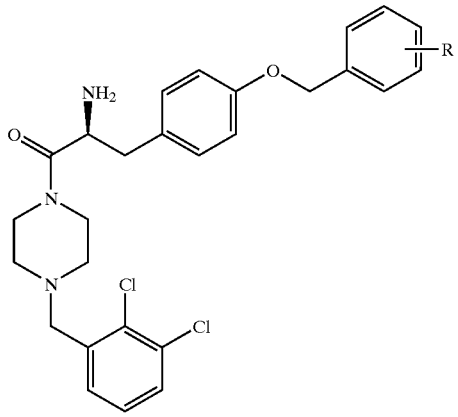

| Example No. | R | M.S. (M + H)+ | Displacement Rate (%) (at 10 μM) | MC4R IC$_{50}$(μM) |
|---|---|---|---|---|
| 227 | 2-CH$_3$O, 5-CH$_3$O | 559 | ++ | C |
| 228 | 2-CH$_3$O, 4-CH$_3$O | 559 | ++ | C |
| 229 | 3,4-(—OCH$_2$O—), 6-NO$_2$ | 588 | ++ | C |
| 230 | 4-(CH$_3$(CH$_2$)$_3$O) | 571 | ++ | B |
| 231 | 2-CH$_3$O | 529 | ++ | C |
| 232 | 2,3-Benzo, 5,6-Benzo | 599 | ++ | C |
| 233 | 2-CH$_3$O, 3-CH$_3$O | 559 | + | C |
| 234 | 3-CH$_3$O, 4-CH$_3$O | 559 | + | C |
| 235 | 3,4-(—OCH$_2$O—) | 543 | + | C |
| 236 | 3-CH$_3$O, 4-CH$_3$O, 5-CH$_3$O | 589 | + | n.t. | n.t. = not testes

TABLE 5

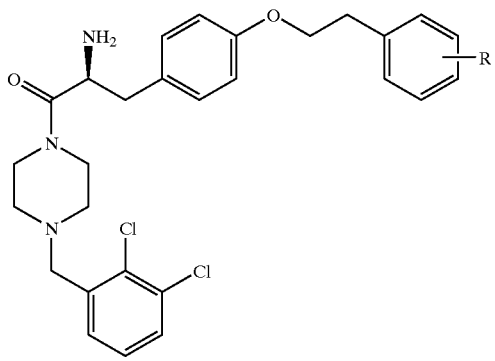

| Example No. | R | M.S. (M + H) | Displacement Rate (%) (at 10 μM) | MC4R IC$_{50}$ (μM) |
|---|---|---|---|---|
| 237 | 2-CH$_3$ | 527 | +++ | A |
| 238 | H | 513 | +++ | A |
| 239 | 4-CH$_3$ | 527 | +++ | A |
| 240 | 3-F | 531 | +++ | A |
| 241 | 4-Br | 591 | +++ | A |
| 242 | 2-Cl | 547 | +++ | A |
| 243 | 3-CH$_3$O | 544 | +++ | A |
| 244 | 2,3-Benzo | 563 | +++ | A |

TABLE 5-continued

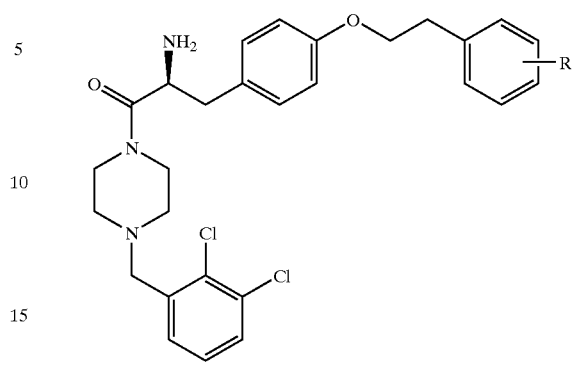

| Example No. | R | M.S. (M + H) | Displacement Rate (%) (at 10 μM) | MC4R IC$_{50}$ (μM) |
|---|---|---|---|---|
| 245 | 4-Cl | 547 | +++ | A |
| 246 | 2-Cl, 4-Cl | 581 | +++ | A |
| 247 | 4-F | 531 | +++ | A |
| 248 | 3-Br | 591 | +++ | A |
| 249 | 3-Cl | 547 | +++ | A |
| 250 | 3-(C$_6$H$_5$CH$_2$O) | 619 | +++ | A |
| 251 | 4-(C$_6$H$_5$CH$_2$O) | 619 | +++ | A |
| 252 | 2-(C$_6$H$_5$CH$_2$O) | 619 | +++ | A |
| 253 | 2-C$_6$H$_5$ | 589 | +++ | A |
| 254 | 4-CH$_3$O | 543 | +++ | A |
| 255 | 3-CF$_3$ | 581 | +++ | A |
| 256 | 3,4-Benzo | 563 | +++ | A |
| 257 | 3-NO$_2$ | 558 | +++ | B |
| 258 | 4-NO$_2$ | 558 | ++ | C |
| 259 | 3-CH$_3$O, 4-CH$_3$O | 573 | + | C |

TABLE 6

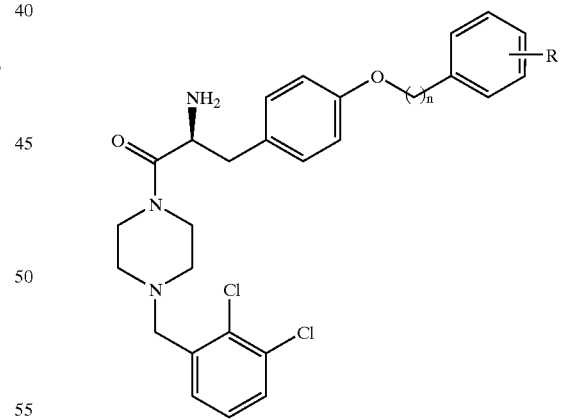

| Example No. | R | n | M.S. (M + H)+ | Displacement Rate (%) (at 10 μM) | MC4R IC$_{50}$ (μM) |
|---|---|---|---|---|---|
| 260 | 4-(C$_6$H$_5$CH$_2$O) | 3 | 633 | +++ | A |
| 261 | H | 3 | 527 | +++ | A |
| 262 | H | 4 | 541 | +++ | A |
| 263 | α-CH$_3$ | 3 | 541 | +++ | A |
| 264 | 4-CH$_3$O | 3 | 557 | ++ | B |
| 265 | 3-CH$_3$O, 4-CH$_3$O | 3 | 587 | ++ | A |

TABLE 7

| Examples No. | R | n | X | M.S. (M + H)+ | Displacement Rate (%) (at 10 μM) | MC4R IC50 (μM) |
|---|---|---|---|---|---|---|
| 266 | H | 2 | O | 543 | +++ | A |
| 267 | 3-CH3 | 1 | O | 543 | +++ | A |
| 268 | H | 1 | O | 529 | +++ | A |
| 269 | 2, 3, 4, 5, 6-F5 | 1 | O | 619 | +++ | A |
| 270 | 2-Cl | 1 | O | 563 | +++ | B |
| 271 | H | 1 | S | 545 | +++ | B |

TABLE 8

| Example No. | R | M.S. (M + H)+ | Displacement Rate (%) (at 10 μM) | MC4R IC50 (μM) |
|---|---|---|---|---|
| 272 | 2-(2-Thienyl)ethyl | 519 | +++ | A |
| 273 | 2-(3-Thienyl)ethyl | 519 | +++ | A |
| 274 | Cyclopentylmethyl | 491 | +++ | A |
| 275 | Cyclohexylmethyl | 519 | +++ | A |
| 276 | n-Hexyl | 493 | +++ | A |
| 277 | 3-(Cyclopentyl)propyl | 519 | +++ | A |
| 278 | 3-Methylbutyl | 479 | +++ | A |
| 279 | 3-Cyclohexylpropyl | 533 | +++ | A |
| 280 | 3,3-Dimethylbutyl | 493 | +++ | A |
| 281 | 4-Cyclohexylbutyl | 547 | +++ | A |
| 282 | N-(3-Methylphenyl)-N-(ethyl)aminoethyl | 571 | +++ | A |
| 283 | (1-Methylethyl)thioethyl | 511 | ++ | B |
| 284 | Cyclopentyl | 477 | +++ | B |
| 285 | N-(Phenylmethyl)-N-(methyl)aminoethyl | 557 | ++ | B |
| 286 | Cyclopropylmethyl | 463 | ++ | C |
| 287 | N-(Phenylmethyl)-N-(methyl)aminopropyl | 571 | + | C |

EXAMPLE 288

3-(4-Biphenyl)-L-alanine, 1-[4-(2,3-dichlorophenyl)methyl)]piperazine amide

Step A: N-(tert-Butoxycarbonyl)-[3-(4-biphenyl)]-L-alanine, 1-[4-(2,3-dichlorophenyl)methyl)]piperazine amide To a 1-dram vial was added consecutively [(N-tert-butyloxycarbonyl)-(3-(4-iodophenyl)-L-alanine)], 1-[4-(2,3-dichlorophenyl)methyl)]piperazine amide [Intermediate (6), (38.7 mg, 0.0626 mmol, in 1 mL EtOH, 1 equiv.)], phenylboronic acid (15.3 mg, 0.125 mmol, 2.0 equiv), Pd(PPh3)4 (1 mg, 0.007 mmol, 0.1 equiv.), EtOH (1 mL), and aqueous Na2CO3 solution (0.15 mL, 2.0 M, 5 equiv.). The vial was tightly sealed with a teflon-lined lid and heated at 90° C. for 2 hours and at 100° C. for 30 minutes. The reaction mixture was then allowed to cool to room temperature, and was then diluted with CH2Cl2 (1 mL) and filtered. The filtrate was concentrated in vacuo, then the residue was purified by flash column chromatography on silica (5:1 CH2Cl2/EtOAc) to afford the titled product (33.5 mg, 94.2%) as a colorless oil: $^1$H NMR (CDCl3) δ 7.61–7.51 (m, 4H), 7.44 (t, J=7.4 Hz, 2H), 7.37–7.31 (m, 2H) 7.27 (d, J=8.7 Hz, 3H), 7.12 (d, J=7.8 Hz, 1H), 5.46 (d, J=8.6 Hz, 1H), 4.86 (q, J=7.7 Hz, 2H), 3.72–3.60 (br, 1H), 3.50–3.09

(m, 5H), 3.06–2.95 (m, 2H), 2.52–2.40 (br, 1H), 2.38–2.20 (br, 2H), 1.80–1.64 (br, 1H), 1.43 (s, 9H); $^{13}$C NMR (CDCl$_3$) δ 170.21, 155.30, 140.95, 140.19, 138.02, 135.76, 133.44, 132.67, 130.30, 129.34, 129.05, 128.62, 127.55, 127.48, 127.21, 79.98, 59.87, 52.77, 51.07, 45.85, 42.23, 40.26, 28.60; MS Calcd for $[C_{31}H_{35}Cl_2N_3O_3+H]^+$: 568. found: 568.

Step B: 3-(4-Biphenyl)-L-alanine, 1-[4-(2,3-dichlorophenyl)methyl)]piperazine amide

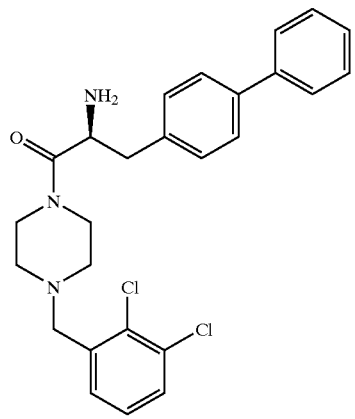

The N-(tert-butoxycarbonyl)-[3-(4-biphenyl)]-L-alanine, 1-[4-(2,3-dichlorophenyl)methyl)]piperazine amide [from Step A, (31.5 mg)] was dissolved in HCl/dioxane (4.0 M, 1 mL) and stirred at room temperature for 2 hours. After concentration in vacuo, the residue was suspended in CH$_2$Cl$_2$ and made basic with aqueous NaOH (10 N). The organic layer was separated, dried over Na$_2$SO$_4$, filtered and the filtrate concentrated in vacuo. The residue was purified by flash column chromatography on silica (20:1 CH$_2$Cl$_2$/ 1.0M NH$_3$ in MeOH) to afford the free base of the titled compound (24.0 mg, 92.3%) as a colorless oil: $^1$H NMR (CDCl$_3$) δ 7.60–7.49 (m, 4H), 7.47–7.40 (m, 2H), 7.38–7.31 (m, 2H), 7.30–7.25 (m, 3H), 7.13 (d, J=7.8 Hz, 1H), 4.03 (t, J=7.2 Hz, 1H), 3.80–3.70 (m, 1H), 3.54–3.43 (m, 3H), 3.39–3.30 (m, 1H), 3.25–3.19 (m, 1H), 2.98 (dd, J=13.2 and 7.4 Hz, 1H), 2.89 (dd, J=13.2 and 7.0 Hz, 1H), 2.54–2.46 (m, 1H), 2.39–2.22 (m, 4H), 1.86–1.78 (m, 1H); $^{13}$C NMR (CDCl$_3$) δ 173.07, 140.96, 140.10, 138.09, 136.78, 133.43, 132.67, 130.11, 129.32, 129.05, 128.64, 127.58, 127.55, 127.21, 127.17, 59.96, 52.89, 52.51, 45.58, 42.68, 42.32; MS Calcd for $[C_{26}H_{27}Cl_2N_3O+H]^+$: 468. found: 468.

EXAMPLES 289–343

Examples 289–343 were synthesized according to the same procedures as described for the synthesis of Example 288 starting from [(N-tert-butyloxycarbonyl)-(3-(4-iodophenyl)-L-alanine)], 1-[4-(2,3-dichlorophenyl)methyl)] piperazine amide (Intermediate 6) and an appropriately substituted phenyl boronic acid or heteroaryl boronic acid (in place of phenyl boronic acid as in Example 288). However, the purification of the intermediates and the final products were made more amenable for parallel synthesis. Thus after the Suzuki coupling reaction (Step A as described in Example 288) was cooled down to room temperature, it was checked by LCMS and found to be complete conversion in most cases. The reaction mixture was then diluted with 1 mL CH$_2$Cl$_2$ and passed through a celite cartridge. The vial was rinsed with CH$_2$Cl$_2$ three times and the CH$_2$Cl$_2$ solution were used to washed the celite cartridge. For reactions which were incomplete or those reactions starting with boronic acids with basic site(s), flash column chromatography on silica or preparative HPLC were used to purify the intermediate products (from Step A as in Example 288). Otherwise the combined organic solution was loaded slowly onto a SCX cartridge and washed with CH$_2$Cl$_2$ and MeOH (3 times each). The individual intermediate product along with some deprotected product were eluted out with NH$_3$/MeOH (2.0 M). After the eluant was concentrated in vacuo, the complete deprotection (as in Step B of Example 288) was effected by treatment with HCl/dioxane for 1 hour followed by concentration in vacuo to afford the HCl salt of the product. For Examples 289–343 LC/MS showed purities >95% and correct molecular masses. The observed mass (M+H)$^+$, and biological activity are provided in Tables 9 and 10.

TABLE 9

| Example No. | R | M.S. (M + H) | Displacement Rate (%) | MC4R IC$_{50}$ (μM) |
|---|---|---|---|---|
| 289 | H | 468 | n.t. | A |
| 290 | 4-CH$_3$ | 482 | +++ | A |
| 291 | 4-CH$_3$CH$_2$ | 496 | +++ | A |
| 292 | 4-CF$_3$O | 552 | +++ | A |
| 293 | 3,4-Benzo | 518 | +++ | A |
| 294 | 3-Cl, 4-Cl | 536 | +++ | A |
| 295 | 4-CH$_3$S | 514 | +++ | A |
| 296 | 4-F | 486 | +++ | A |
| 297 | 3-CF$_3$, 5-CF$_3$ | 604 | +++ | A |
| 298 | 4-Cl | 502 | +++ | A |
| 299 | 2-Cl, 3-Cl | 536 | +++ | A |
| 300 | 2,3-Benzo | 518 | +++ | A |
| 301 | 3-Cl | 502 | +++ | A |
| 302 | 4-PhO | 560 | +++ | A |
| 303 | 3-(CH$_3$)$_2$ | 510 | +++ | A |
| 304 | 4-CF$_3$ | 536 | +++ | A |
| 305 | 4-(CH$_3$)$_3$C | 524 | +++ | A |
| 306 | 3-Cl, 4-F | 520 | +++ | A |
| 307 | 2-Cl, 4-Cl | 536 | +++ | A |
| 308 | 3-CH$_3$CH$_2$O | 512 | +++ | A |
| 309 | 2-F | 486 | +++ | A |
| 310 | 4-CH$_3$CH$_2$O | 512 | +++ | A |
| 311 | 3-F | 486 | +++ | A |
| 312 | 3-Cl, 5-Cl | 536 | +++ | B |
| 313 | 2-CH$_3$ | 482 | +++ | B |
| 314 | 4-Ph | 544 | +++ | B |
| 315 | 2-CF$_3$ | 536 | +++ | B |
| 316 | 2-CH$_3$CH$_2$ | 512 | +++ | B |
| 317 | 4-CH$_3$O | 498 | +++ | B |
| 318 | 3-CH$_3$ | 482 | +++ | B |
| 319 | 3,4-(—OCH$_2$O—) | 512 | ++ | B |
| 320 | 2-CH$_3$O, 5-CH$_3$O | 528 | +++ | B |
| 321 | 2-Cl | 502 | +++ | B |
| 322 | 2-CH$_3$O, 4-CH$_3$O | 528 | ++ | B |
| 323 | 4-(CH$_3$)$_2$N | 511 | ++ | B |
| 324 | 2-Cl, 6-Cl | 536 | +++ | B |
| 325 | 3-CH$_3$O | 498 | ++ | B |
| 326 | 2-CH$_3$O | 498 | ++ | B |

TABLE 9-continued

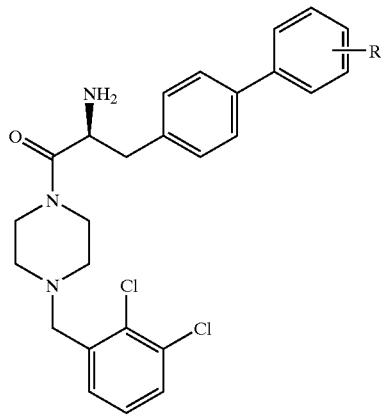

| Example No. | R | M.S. (M + H) | Displacement Rate (%) | MC4R IC$_{50}$ (μM) |
|---|---|---|---|---|
| 327 | 3-Cl, 6-CH$_3$O | 532 | +++ | B |
| 328 | 3-CH$_3$CO | 510 | ++ | B |
| 329 | 4-CO$_2$H | 512 | ++ | C |
| 330 | 3-NO$_2$ | 513 | ++ | C |
| 331 | 3-CH$_3$O, 4-CH$_3$O | 528 | + | C |
| 332 | 4-(CH$_3$)$_2$CH | 510 | + | C |
| 333 | 3-NH$_2$ | 483 | ++ | C |
| 334 | 3-CH$_3$O, 4-CH$_3$O, 5-CH$_3$O, | 558 | + | C | n.t. = not tested

TABLE 10

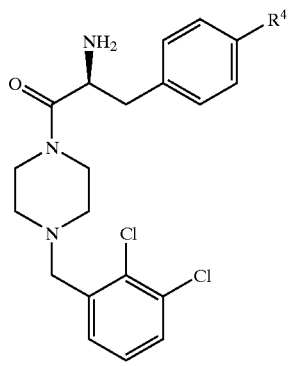

| Example No. | R$^4$ | M.S. (M + H)$^+$ | Displacement Rate (%) (at 10 μM) | MC4R IC$_{50}$(μM) |
|---|---|---|---|---|
| 335 | 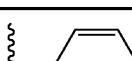 | 590 | +++ | A |

TABLE 10-continued

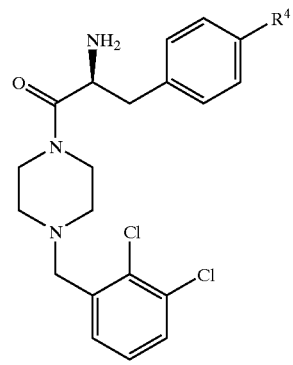

| Example No. | R$^4$ | M.S. (M + H)$^+$ | Displacement Rate (%) (at 10 μM) | MC4R IC$_{50}$(μM) |
|---|---|---|---|---|
| 336 | 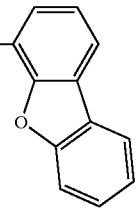 | 558 | +++ | A |
| 337 | 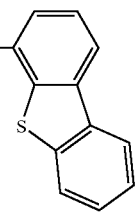 | 574 | +++ | A |
| 338 | 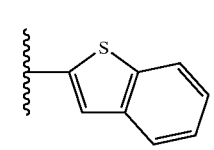 | 524 | +++ | A |
| 339 | 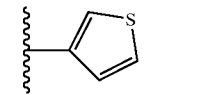 | 474 | +++ | A |
| 340 | 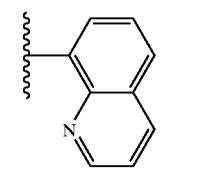 | 519 | ++ | B |
| 341 | 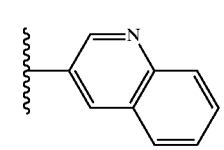 | 519 | ++ | B |
| 342 | 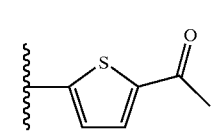 | 516 | ++ | B |

TABLE 10-continued

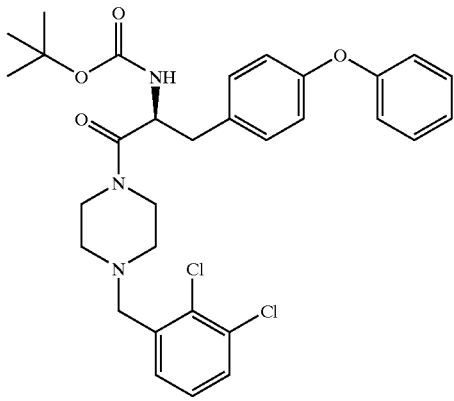

| Example No. | R[4] | M.S. (M + H)[+] | Displacement Rate (%) (at 10 μM) | MC4R IC$_{50}$(μM) |
|---|---|---|---|---|
| 343 | ![pyridyl-OMe] | 499 | + | C |

EXAMPLE 344

O-Phenyl-L-tyrosine, 1-[4-(2,3-dichlorophenyl)methyl)]-piperazine amine

Step A: (N-tert-Butyloxycarbonyl)-O-phenyl-L-tyrosine, 1-[4-(2,3-dichlorophenyl)methyl)]piperazine amide

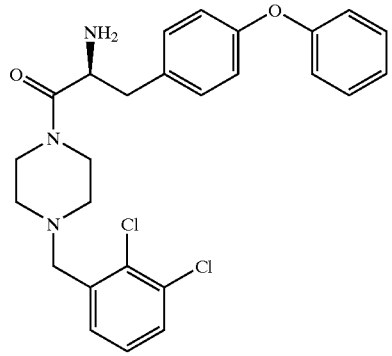

A mixture of N-(tert-butyloxycarbonyl)-L-tyrosine, 1-[4-[(2,3-dichlorophenyl)methyl)]piperazine]amide [Intermediate (5), (32.0 mg, 0.0629 mmol, 1.0 equiv.)], phenylboronic acid (15.4 mg, 0.126 mmol, 2.0 equiv.), Cu(OAc)$_2$ (11.4 mg, 0.0629 mmol, 1.0 equiv.), pyridine (26 μL, 5.0 equiv.) and some crushed molecular sieves was suspended in CH$_2$Cl$_2$ and stirred at room temperature for 18 hours. Analysis by LC/MS showed complete conversion. The mixture was then filtered through a cotton plug and purified by flash column chromatography on silica (eluted with 5:1 CH$_2$Cl$_2$/EtOAc) to afford the titled bisphenylether product (31 mg, 84.2%) as a colorless oil: $^1$H NMR (CDCl$_3$) δ 7.39–7.27 (m, 4H), 7.18–6.97 (m, 4H), 6.95–6.91 (m, 4H), 5.45 (d, J=8.5 Hz, 1H), 4.81 (q, J=7.6 Hz, 1H 3.70 (br, 4H), 3.58 (br, 1H), 3.39 (br, 1H), 2.94 (d, J=7.1 Hz, 2H), 2.46–2.37 (br, 3H), 2.04 (br, 1H), 1.42 (s, 9H); $^{13}$C NMR (CDCl$_3$) δ 170.25, 157.45, 156.54, 155.28, 133.55, 132.79, 131.54, 131.09, 129.97, 129.47, 128.81, 127.26, 123.49, 119.16, 119.03, 79.96, 59.91, 52.95, 52.74, 51.20, 45.81, 42.20, 39.75, 28.59; MS Calcd for [C$_{31}$H$_{35}$Cl$_2$N$_3$O$_4$+H]$^+$: 584. found: 584.

Step B: O-Phenyl-L-tyrosine, 1-[4-(2,3-dichlorophenyl)methyl)]-piperazine amide

The tert-butyloxycarbonyl protected bisphenylether [product from Step A, (29 mg)] was dissolved in HCl/dioxane (4.0 M, 1 mL) and stirred at room temperature for 2 hours. After concentration in vacuo, the residue was suspended in CH$_2$Cl$_2$ and made basic with aqueous NaOH (10 N). The organic layer was separated, dried over Na$_2$SO$_4$, filtered and the filtrate was concentrated in vacuo. The residue was purified by flash column chromatography on silica (20:1 CH$_2$Cl$_2$/1.0M NH$_3$ in MeOH) to afford the free base of the titled product (23.2 mg, 96.7%) as a colorless oil: $^1$H NMR (CDCl$_3$) δ 7.40–7.25 (m, 4H), 7.13–7.06 (m, 4H), 7.01–6.91 (m, 4H), 3.97 (t, J=7.1 Hz, 1H), 3.68–3.54 (m, 4H), 3.43–3.35 (m, 1H), 3.22–3.14 (m, 1H), 2.92 (dd, J=13.4 and 7.2 Hz, 1H), 2.81 (dd, J=13.4 and 7.0 Hz, 1H), 2.52–2.33 (m, 3H), 2.13–2.03 (m, 3H); $^{13}$C NMR (CDCl$_3$) δ 173.11, 157.43, 156.47, 138.09, 133.51, 132.76, 132.53, 130.90, 129.98, 129.40, 128.75, 127.22, 123.52, 119.22, 119.05, 60.03, 53.05, 52.93, 52.60, 45.56, 42.28, 42.21; MS Calcd for [C$_{26}$H$_{27}$Cl$_2$N$_3$O$_2$+H]$^+$: 484. found: 484.

EXAMPLES 345–348

General Procedure. Parallel synthesis of Examples 345–348 followed the same initial synthetic procedure as described above for the synthesis of Example 344 (Step A) starting from intermediate 5 and the appropriately substituted phenylboronic acid. The workup was modified however, as the intermediate products of Step A were not purified. Instead, each individual reaction mixture was filtered through a cotton plug and passed through a pre-wetted (with saturated Cu$_2$SO$_4$ solution) celite cartridge. The cartridge was rinsed twice with CH$_2$Cl$_2$. The combined CH$_2$Cl$_2$ solution was then concentrated in vacuo and treated with HCl/dioxane (4 M) for 2 hours. After concentration in vacuo, the residue was dissolved in MeOH and purified by preparative HPLC. The purified yields for Examples 345–348 were above 60% overall for the two steps of the synthesis. The observed molecular mass (M+H)+, and biological activity are provided in Table 11.

TABLE 11

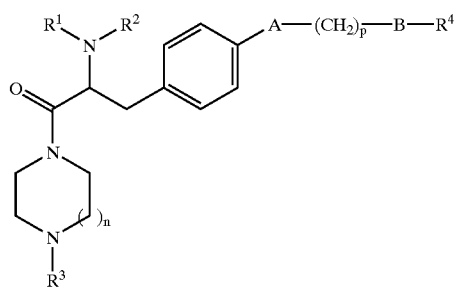

| Example No. | R | M.S. (M + H)+ | Displacement Rate | MC4R IC$_{50}$($\mu$M) |
|---|---|---|---|---|
| 344 | 4-H | 484 | n.t. | C |
| 345 | 4-Me | 498 | n.t. | A |
| 346 | 3,-Cl, 4-Cl | 552 | n.t. | B |
| 347 | 3-Me | 498 | n.t. | B |
| 348 | 2-Me | 498 | n.t. | B | n.t. = not tested

What is claimed is:

1. A compound of Formula I, or a pharmaceutically acceptable salt thereof

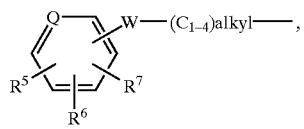

I wherein n is 1;

p is selected from an integer of 0 to 4;

A is a bond or O;

B is selected from the group consisting of a bond, O, S, NH and —N(C$_{1-4}$)alkyl;

R$^1$ and

R$^2$ each are independently selected from the group consisting of hydrogen, (C$_{1-4}$)alkyl, phenyl(C$_{1-4}$)alkyl, imidazolyl(C$_{1-4}$)alkyl, imidazolyl(C$_{1-4}$)alkylcarbonyl, imidazyloarbonyl, morpholinyl(C$_{1-4}$)alkyl, piperidinyl(C$_{1-4}$)alkyl, and di(C$_{1-4}$)alkylamino(C$_{1-4}$) alkyl;

R$^3$ is selected from the group consisting of (C$_{1-8}$)alkyl,

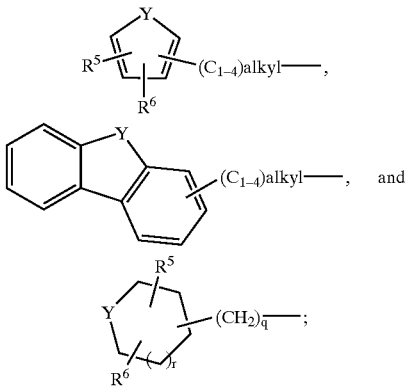

Q is N or CR$^8$,

W is selected from the group consisting of a bond, NH, O, S, and C$_6$H$_5$CH;

Y is selected from the group consisting of CHR$^{11}$, NR$^{11}$, O, and S;

q is 0 or 1;

r is 0 or 1;

R$^4$ is selected from the group consisting of C$_{1-4}$alkyl, C$_{3-7}$cycloalkyl, phenyl, phenyl(C$_{1-4}$alkyl, napthalenyl, benzodioxolyl, benzodioxanyl, pyridinyl, quinolinyl, thienyl, benzothienyl, dibenzothienyl, and phenoxathiinyl; and wherein said phenyl, thienyl and pyridyl are optionally substituted with one to three substituents each independently selected from halogen, trifluoromethyl, trifluoromethoxy, nitro, C$_{1-4}$alkyl, C$_{1-4}$alkoxy, C$_{1-4}$thioalkoxy, C$_{1-4}$alkylcarbonyl, di(C$_{1-4}$ alkyl)amino, amino, carboxyl, phenyl, phenyl(C$_{1-4}$) alkyl, phenyloxy, and phenylmethoxy;

R$^5$, R$^6$, R$^7$ and

R$^8$ each are independently selected from the group consisting of hydrogen, halogen, C$_{1-8}$alkyl, trifluoromethyl, nitro, XR$^9$, phenyl, and phenyl(C$_{2-6}$) alkenyl, wherein said phenyl is optionally substituted with one to two halogen or nitro groups; or any two variables selected from the group consisting of R$^5$, R$^6$, R$^7$ and R$^8$, when attached to adjacent carbon atoms in a ring containing Q or Y and taken together can be —OCH$_2$O—, —O(CH$_2$)$_2$O—, —CH=CH—CH=CH—, or —CH=CH—N(R$^{11}$)—;

X is selected from the group consisting of NR$^{10}$, O, and S(O)$_m$, wherein m is 0, 1, or 2;

R$^9$ is selected from the group consisting of hydrogen, C$_{1-8}$alkyl, phenyl, phenyl(C$_{1-4}$)alkyl, and wherein said phenyl and phenyl(C$_{1-4}$)alkyl are optionally substituted with one to three substituents each independently selected from nitro, trifluoromethyl, halogen and C$_{1-4}$alkyl;

R$^{10}$ is selected from the group consisting of hydrogen, C$_{1-8}$alkyl, and phenyl; and R$^{11}$ is selected from the group consisting of hydrogen, C$_{1-4}$alkyl, C$_{1-4}$alkylsulfonyl, phenyl, phenyl(C$_{1-4}$) alkyl, and phenylsulfonyl, wherein said phenyl, phenyl (C$_{1-4}$)alkyl, and phenylsulfonyl are optionally substituted with one to three substituents each independently selected from C$_{1-4}$alkyl or halogen.

2. The compound according to claim 1, or a pharmaceutically acceptable salt thereof,

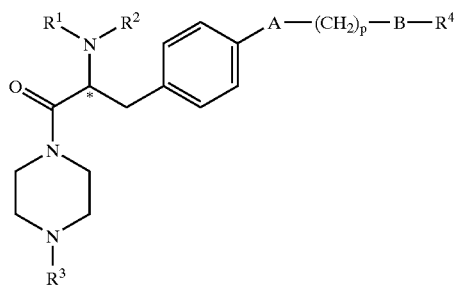

wherein the stereochemistry of the chiral carbon marked by the * has the S configuration.

3. The compound according to claim 2, or a pharmaceutically acceptable salt thereof, wherein $R^3$ is

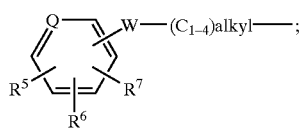

and Q is $CR^8$.

4. The compound according to claim 3, or a pharmaceutically acceptable salt thereof, wherein A is O; and $R^4$ is phenyl; wherein said phenyl is optionally substituted with one to three substituents each independently selected from halogen, trifluoromethyl, trifluoromethoxy, nitro, $C_{1-4}$alkyl, $C_{1-4}$alkoxy, $C_{1-4}$thioalkoxy, $C_{1-4}$alkylcarbonyl, di($C_{1-4}$alkyl)amino, amino, carboxyl, phenyl, phenyl($C_{1-4}$alkyl, phenyloxy, and phenylmethoxy.

5. The compound according to claim 3, or a pharmaceutically acceptable salt thereof, wherein p is 0; A and B taken together are a bond; and $R^4$ is selected from the group consisting of phenyl, napthalenyl, benzodioxolyl, benzodioxanyl, pyridinyl, quinolinyl, thienyl, benzothienyl, dibenzothienyl, and phenoxathiinyl; and wherein said phenyl, thienyl and pyridyl are optionally substituted with one to three substituents each independently selected from halogen, trifluoromethyl, trifluoromethoxy, nitro, $C_{1-4}$alkyl, $C_{1-4}$alkoxy, $C_{1-4}$thioalkoxy, $C_{1-4}$alkylcarbonyl, di($C_{1-4}$alkyl)amino, amino, carboxyl, phenyl, phenyl($C_{1-4}$)alkyl, phenyloxy, and phenylmethoxy.

6. A pharmaceutical composition which comprises a compound as claimed in claim 1 and a pharmaceutically acceptable carrier, adjuvant or diluent.

7. A method for the treatment of disorder, diseases or conditions responsive to the activation of melanocortin receptor wherein said disorder, disease or condition is obesity which comprises administering to a mammal in need of such treatment a therapeutically effective amount of a compound as claimed in claim 1.

* * * * *